United States Patent
Meadows et al.

(10) Patent No.: US 8,428,725 B2
(45) Date of Patent: Apr. 23, 2013

(54) METHOD OF STIMULATING A HYPOGLOSSAL NERVE FOR CONTROLLING THE POSITION OF A PATIENT'S TONGUE

(75) Inventors: Paul M. Meadows, Glendale, CA (US); Marcelo G. Lima, San Diego, CA (US); Faisal N. Zaidi, San Diego, CA (US)

(73) Assignee: Imthera Medical, Inc., San Diego, CA (US)

( * ) Notice: Subject to any disclaimer, the term of this patent is extended or adjusted under 35 U.S.C. 154(b) by 744 days.

(21) Appl. No.: 12/572,758

(22) Filed: Oct. 2, 2009

(65) Prior Publication Data

US 2010/0094379 A1 Apr. 15, 2010

Related U.S. Application Data

(60) Provisional application No. 61/136,857, filed on Oct. 9, 2008, provisional application No. 61/161,715, filed on Mar. 19, 2009, provisional application No. 61/179,529, filed on May 19, 2009.

(51) Int. Cl.
 *A61N 1/36* (2006.01)
(52) U.S. Cl.
 USPC .................................. 607/42; 607/2
(58) Field of Classification Search .......... 607/66, 607/48, 42, 2
 See application file for complete search history.

(56) References Cited

U.S. PATENT DOCUMENTS

| | | |
|---|---|---|
| 4,424,812 A | 1/1984 | Lesnick |
| 4,602,624 A | 7/1986 | Naples et al. |
| 5,094,242 A | 3/1992 | Gleason et al. |
| 5,095,905 A | 3/1992 | Klepinski |
| 5,123,425 A | 6/1992 | Shannon, Jr. et al. |
| 5,133,354 A | 7/1992 | Kallok |
| 5,146,918 A | 9/1992 | Kallok et al. |
| 5,158,080 A | 10/1992 | Kallok |

(Continued)

FOREIGN PATENT DOCUMENTS

| | | |
|---|---|---|
| EP | 1524007 | 4/2005 |
| EP | 2116274 A2 | 11/2009 |

(Continued)

OTHER PUBLICATIONS

Fairbanks, David W., M.D.; Fairbanks, David N. F., M.D.; Neurostimulation for Obstructive Sleep Apnea: Investigations; ENT Journal; Jan. 1993; pp. 52-57; vol. 72, No. 1; International Pub. Group; Cleveland, OH.

(Continued)

*Primary Examiner* — Carl H Layno
*Assistant Examiner* — Jon Eric C Morales
(74) *Attorney, Agent, or Firm* — Morgan, Lewis & Bockius LLP

(57) ABSTRACT

A method for controlling a position of a patient's tongue includes attaching at least one electrode to the patient's Hypoglossal nerve and applying an electric signal through the electrode to at least one targeted motor efferent located within the Hypoglossal nerve to stimulate at least one muscle of the tongue. Methods may also include the use of more than one contact to target more than one motor efferent and stimulating more than one muscle. The stimulation load to maintain the position of the tongue may be shared by each muscle. The position of the patient's tongue may be controlled in order to prevent obstructive sleep apnea.

13 Claims, 9 Drawing Sheets

U.S. PATENT DOCUMENTS

| | | |
|---|---|---|
| 5,174,287 A | 12/1992 | Kallok et al. |
| 5,190,053 A | 3/1993 | Meer |
| 5,211,173 A | 5/1993 | Kallok et al. |
| 5,215,082 A | 6/1993 | Kallok et al. |
| 5,233,983 A | 8/1993 | Markowitz |
| 5,281,219 A | 1/1994 | Kallok |
| 5,300,094 A | 4/1994 | Kallok et al. |
| 5,344,438 A | 9/1994 | Testerman et al. |
| 5,483,969 A | 1/1996 | Testerman et al. |
| 5,522,862 A | 6/1996 | Testerman et al. |
| 5,540,731 A | 7/1996 | Testerman |
| 5,540,732 A | 7/1996 | Testerman |
| 5,540,733 A | 7/1996 | Testerman et al. |
| 5,545,201 A | 8/1996 | Helland et al. |
| 5,546,952 A | 8/1996 | Erickson |
| 5,591,216 A | 1/1997 | Testerman et al. |
| 5,713,922 A | 2/1998 | King |
| 5,771,891 A | 6/1998 | Gozani |
| 5,837,006 A | 11/1998 | Ocel et al. |
| 5,871,512 A | 2/1999 | Hemming et al. |
| 5,944,680 A * | 8/1999 | Christopherson et al. ...... 602/42 |
| 5,988,171 A | 11/1999 | Sohn et al. |
| 6,021,352 A | 2/2000 | Christopherson et al. |
| 6,051,017 A | 4/2000 | Loeb et al. |
| 6,132,384 A | 10/2000 | Christopherson et al. |
| 6,175,767 B1 | 1/2001 | Doyle, Sr. |
| 6,212,435 B1 | 4/2001 | Lattner et al. |
| 6,240,316 B1 | 5/2001 | Richmond et al. |
| 6,251,126 B1 | 6/2001 | Ottenhoff et al. |
| 6,266,560 B1 | 7/2001 | Zhang et al. |
| 6,269,269 B1 | 7/2001 | Ottenhoff et al. |
| 6,345,202 B2 | 2/2002 | Richmond et al. |
| 6,408,852 B2 | 6/2002 | Tielemans |
| 6,409,676 B2 | 6/2002 | Ruton et al. |
| 6,415,174 B1 | 7/2002 | Bebehani et al. |
| 6,427,689 B1 | 8/2002 | Estes et al. |
| 6,432,956 B1 | 8/2002 | Dement et al. |
| 6,454,724 B1 | 9/2002 | Greene |
| 6,456,866 B1 | 9/2002 | Tyler et al. |
| 6,475,156 B1 | 11/2002 | Vega |
| 6,488,634 B1 | 12/2002 | Rapoport et al. |
| 6,516,802 B2 | 2/2003 | Hansen et al. |
| 6,516,805 B1 | 2/2003 | Thornton |
| 6,529,752 B2 | 3/2003 | Krausman et al. |
| 6,536,439 B1 | 3/2003 | Palmisano |
| 6,555,564 B1 | 4/2003 | Radulovacki et al. |
| 6,572,543 B1 | 6/2003 | Christopherson et al. |
| 6,574,507 B1 | 6/2003 | Bonnet |
| 6,580,944 B1 | 6/2003 | Katz et al. |
| 6,586,478 B2 | 7/2003 | Ackman et al. |
| 6,587,725 B1 | 7/2003 | Durand et al. |
| 6,594,370 B1 | 7/2003 | Anderson |
| 6,595,215 B2 | 7/2003 | Wood |
| 6,613,779 B2 | 9/2003 | Mondadori et al. |
| 6,629,527 B1 | 10/2003 | Estes et al. |
| 6,635,021 B1 | 10/2003 | Sullivan et al. |
| 6,636,767 B1 | 10/2003 | Knudson et al. |
| 6,641,542 B2 | 11/2003 | Cho et al. |
| 6,658,301 B2 | 12/2003 | Loeb et al. |
| 6,666,830 B1 | 12/2003 | Lehrman et al. |
| 6,671,907 B1 | 1/2004 | Zuberi |
| 6,705,315 B2 | 3/2004 | Sullivan et al. |
| 6,727,242 B2 | 4/2004 | Radulovacki et al. |
| 6,729,335 B1 | 5/2004 | Halstrom |
| 6,731,984 B2 | 5/2004 | Cho et al. |
| 6,752,766 B2 | 6/2004 | Kowallik et al. |
| 6,761,167 B1 | 7/2004 | Nadjafizadeh et al. |
| 6,761,168 B1 | 7/2004 | Nadjafizadeh et al. |
| 6,766,802 B1 | 7/2004 | Keropian |
| 6,770,022 B2 | 8/2004 | Mechlenburg et al. |
| 6,770,037 B2 | 8/2004 | Sullivan et al. |
| 6,773,404 B2 | 8/2004 | Poezevera et al. |
| 6,776,162 B2 | 8/2004 | Wood |
| 6,788,975 B1 | 9/2004 | Whitehurst et al. |
| 6,793,629 B2 | 9/2004 | Rapoport et al. |
| 6,807,967 B2 | 10/2004 | Wood |
| 6,811,538 B2 | 11/2004 | Westbrook et al. |
| 6,814,074 B1 | 11/2004 | Nadjafizadeh et al. |
| 6,818,665 B2 | 11/2004 | Wennerholm et al. |
| 6,835,740 B2 | 12/2004 | Rubin et al. |
| 6,857,149 B2 | 2/2005 | Hoggatt et al. |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,893,405 B2 | 5/2005 | Kumar et al. |
| 6,901,292 B2 | 5/2005 | Hrdlicka et al. |
| 6,904,320 B2 | 6/2005 | Park et al. |
| 6,918,394 B2 | 7/2005 | Matsuda et al. |
| 6,928,324 B2 | 8/2005 | Park et al. |
| 6,964,641 B2 | 11/2005 | Cho et al. |
| 6,999,819 B2 | 2/2006 | Swoyer et al. |
| 7,003,352 B1 | 2/2006 | Whitehurst |
| 7,092,763 B1 | 8/2006 | Griffith et al. |
| 7,184,836 B1 | 2/2007 | Meadows et al. |
| 7,245,971 B2 | 7/2007 | Park et al. |
| 7,570,997 B2 | 8/2009 | Lovett et al. |
| 7,644,714 B2 | 1/2010 | Atkinson et al. |
| 7,680,538 B2 | 3/2010 | Durand et al. |
| 7,725,195 B2 | 5/2010 | Lima et al. |
| 7,809,442 B2 | 10/2010 | Bolea et al. |
| 2001/0000346 A1 | 4/2001 | Ruton et al. |
| 2001/0001125 A1 | 5/2001 | Schulman et al. |
| 2001/0010010 A1 | 7/2001 | Richmond et al. |
| 2001/0015204 A1 | 8/2001 | Hansen et al. |
| 2001/0018557 A1 | 8/2001 | Lynn et al. |
| 2001/0027793 A1 | 10/2001 | Tielemans |
| 2001/0041719 A1 | 11/2001 | Mondadori et al. |
| 2001/0046988 A1 | 11/2001 | Iglehart |
| 2002/0007127 A1 | 1/2002 | Sullivan et al. |
| 2002/0015740 A1 | 2/2002 | Ackman et al. |
| 2002/0037533 A1 | 3/2002 | Civelli et al. |
| 2002/0049479 A1 | 4/2002 | Pitts |
| 2002/0059935 A1 | 5/2002 | Wood |
| 2002/0086870 A1 | 7/2002 | Radulovacki et al. |
| 2002/0092527 A1 | 7/2002 | Wood |
| 2002/0095076 A1 | 7/2002 | Krausman et al. |
| 2002/0099033 A1 | 7/2002 | Meyer et al. |
| 2002/0100477 A1 | 8/2002 | Sullivan et al. |
| 2002/0124848 A1 | 9/2002 | Sullivan et al. |
| 2002/0124849 A1 | 9/2002 | Billette De Villemeur et al. |
| 2002/0144684 A1 | 10/2002 | Moone |
| 2002/0144685 A1 | 10/2002 | Ivanovich et al. |
| 2002/0165246 A1 | 11/2002 | Holman |
| 2002/0165462 A1 | 11/2002 | Westbrook et al. |
| 2002/0169384 A1 | 11/2002 | Kowallik et al. |
| 2002/0173707 A1 | 11/2002 | Lynn et al. |
| 2002/0175821 A1 | 11/2002 | Ruppel |
| 2002/0183306 A1 | 12/2002 | Howard, Jr. |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0015198 A1 | 1/2003 | Heeke et al. |
| 2003/0021772 A1 | 1/2003 | Birkmayer |
| 2003/0053956 A1 | 3/2003 | Hofmann |
| 2003/0055346 A1 | 3/2003 | Rapoport et al. |
| 2003/0055348 A1 | 3/2003 | Chazal et al. |
| 2003/0056785 A1 | 3/2003 | Narihiko et al. |
| 2003/0083241 A1 | 5/2003 | Young |
| 2003/0093131 A1 | 5/2003 | Loeb et al. |
| 2003/0130266 A1 | 7/2003 | Radulovacki et al. |
| 2003/0130589 A1 | 7/2003 | Poezevera |
| 2003/0139680 A1 | 7/2003 | Sheldon |
| 2003/0139691 A1 | 7/2003 | Kumar et al. |
| 2003/0139789 A1 | 7/2003 | Tvinnereim et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0167018 A1 | 9/2003 | Wyckoff |
| 2003/0172462 A1 | 9/2003 | Hoggatt et al. |
| 2003/0176788 A1 | 9/2003 | Crutchfield et al. |
| 2003/0181958 A1 | 9/2003 | Dobak, III |
| 2003/0183227 A1 | 10/2003 | Klemperer |
| 2003/0195140 A1 | 10/2003 | Ackman et al. |
| 2003/0195571 A1 | 10/2003 | Burnes et al. |

| | | | | | | |
|---|---|---|---|---|---|---|
| 2003/0204213 | A1 | 10/2003 | Jensen et al. | 2006/0149337 A1 | 7/2006 | John |
| 2003/0216789 | A1 | 11/2003 | Deem et al. | 2006/0212096 A1 | 9/2006 | Stevenson |
| 2003/0232839 | A1 | 12/2003 | Hangauer et al. | 2006/0224211 A1 | 10/2006 | Durand et al. |
| 2003/0235313 | A1 | 12/2003 | Kurzweil et al. | 2007/0021794 A1 | 1/2007 | Kieval et al. |
| 2003/0236228 | A1 | 12/2003 | Radulovacki et al. | 2007/0043398 A1 | 2/2007 | Ternes et al. |
| 2004/0002516 | A1 | 1/2004 | Mondadori et al. | 2007/0055308 A1 | 3/2007 | Haller et al. |
| 2004/0002742 | A1 | 1/2004 | Florio | 2007/0066997 A1 | 3/2007 | He et al. |
| 2004/0006339 | A1 | 1/2004 | Underwood et al. | 2007/0100399 A1 | 5/2007 | Parramon et al. |
| 2004/0006375 | A1 | 1/2004 | Poezevera | 2007/0100411 A1 | 5/2007 | Bonde |
| 2004/0016433 | A1 | 1/2004 | Estes et al. | 2007/0129768 A1 | 6/2007 | He et al. |
| 2004/0020493 | A1 | 2/2004 | Wood | 2007/0150006 A1 | 6/2007 | Libbus et al. |
| 2004/0025885 | A1 | 2/2004 | Payne, Jr. | 2007/0150022 A1 | 6/2007 | Ujhazy et al. |
| 2004/0029869 | A1 | 2/2004 | Iglehart, III | 2007/0173893 A1 | 7/2007 | Pitts |
| 2004/0030224 | A1 | 2/2004 | Sotos et al. | 2007/0179557 A1 | 8/2007 | Maschino et al. |
| 2004/0055597 | A1 | 3/2004 | Virr et al. | 2007/0233204 A1 | 10/2007 | Lima et al. |
| 2004/0059240 | A1 | 3/2004 | Cho et al. | 2007/0255366 A1 | 11/2007 | Gerber et al. |
| 2004/0082519 | A1 | 4/2004 | Hedner et al. | 2007/0255367 A1 | 11/2007 | Gerber et al. |
| 2004/0087866 | A1 | 5/2004 | Bowman et al. | 2007/0288064 A1 | 12/2007 | Butson et al. |
| 2004/0087878 | A1 | 5/2004 | Krausman et al. | 2008/0021506 A1 | 1/2008 | Grocela |
| 2004/0097871 | A1 | 5/2004 | Yerushalmy | 2008/0039904 A1 | 2/2008 | Bulkes et al. |
| 2004/0111041 | A1 | 6/2004 | Ni et al. | 2008/0039916 A1 | 2/2008 | Colliou et al. |
| 2004/0127572 | A1 | 7/2004 | Carley et al. | 2008/0091246 A1 | 4/2008 | Carey et al. |
| 2004/0134491 | A1 | 7/2004 | Pflueger et al. | 2008/0097554 A1 | 4/2008 | Payne et al. |
| 2004/0138719 | A1 | 7/2004 | Cho et al. | 2008/0103407 A1 | 5/2008 | Bolea et al. |
| 2004/0144391 | A1 | 7/2004 | Brady et al. | 2008/0103544 A1 | 5/2008 | Weiner |
| 2004/0146873 | A1 | 7/2004 | Ptacek et al. | 2008/0103545 A1 * | 5/2008 | Bolea et al. .................... 607/42 |
| 2004/0157813 | A1 | 8/2004 | Wennerholm et al. | 2008/0109047 A1 | 5/2008 | Pless |
| 2004/0176695 | A1 | 9/2004 | Poezevara | 2008/0114230 A1 | 5/2008 | Addis |
| 2004/0176809 | A1 | 9/2004 | Cho et al. | 2008/0139913 A1 | 6/2008 | Schulman |
| 2004/0186523 | A1 | 9/2004 | Florio | 2008/0172109 A1 | 7/2008 | Rahman et al. |
| 2004/0187873 | A1 | 9/2004 | Brown | 2008/0288025 A1 | 11/2008 | Peterson |
| 2004/0200472 | A1 | 10/2004 | Gold | 2009/0118796 A1 | 5/2009 | Chen et al. |
| 2004/0210261 | A1 | 10/2004 | King et al. | 2009/0210042 A1 | 8/2009 | Kowalczewski |
| 2004/0215095 | A1 | 10/2004 | Lee et al. | 2009/0270904 A1 | 10/2009 | Birk et al. |
| 2004/0225226 | A1 | 11/2004 | Lehrman et al. | 2010/0139667 A1 | 6/2010 | Atkinson et al. |
| 2004/0235807 | A1 | 11/2004 | Weinrich et al. | 2011/0112601 A1 | 5/2011 | Meadows et al. |
| 2004/0254493 | A1 | 12/2004 | Chervin et al. | 2011/0213438 A1 | 9/2011 | Lima et al. |
| 2005/0008587 | A1 | 1/2005 | Schulz et al. | | | |
| 2005/0015117 | A1 | 1/2005 | Gerber | FOREIGN PATENT DOCUMENTS | | |
| 2005/0016536 | A1 | 1/2005 | Rapoport et al. | WO 9900058 A1 | 1/1999 | |
| 2005/0020930 | A1 | 1/2005 | Salisbury et al. | WO 02087433 A1 | 11/2002 | |
| 2005/0022821 | A1 | 2/2005 | Jeppesen | WO 2007092330 A1 | 8/2007 | |
| 2005/0027207 | A1 | 2/2005 | Westbrook et al. | WO 2007098200 A2 | 8/2007 | |
| 2005/0031688 | A1 | 2/2005 | Ayala | WO 2007098202 A2 | 8/2007 | |
| 2005/0034730 | A1 | 2/2005 | Wood | WO 2007117232 A1 | 10/2007 | |
| 2005/0038013 | A1 | 2/2005 | Gold | WO 2007140584 A1 | 12/2007 | |
| 2005/0039757 | A1 | 2/2005 | Wood | WO 2008005903 A2 | 1/2008 | |
| 2005/0042589 | A1 | 2/2005 | Hatlestad et al. | WO 2008039921 A2 | 4/2008 | |
| 2005/0043645 | A1 | 2/2005 | Ono et al. | WO 2008046190 A1 | 4/2008 | |
| 2005/0043652 | A1 | 2/2005 | Lovett et al. | WO 2008048471 A2 | 4/2008 | |
| 2005/0045190 | A1 | 3/2005 | Bennett | WO 2008049199 A1 | 5/2008 | |
| 2005/0048538 | A1 | 3/2005 | Mignot et al. | WO 2009048580 A1 | 4/2009 | |
| 2005/0061315 | A1 | 3/2005 | Lee et al. | WO 2009048581 A1 | 4/2009 | |
| 2005/0061320 | A1 | 3/2005 | Lee et al. | WO 2009140636 A2 | 11/2009 | |
| 2005/0061326 | A1 | 3/2005 | Payne, Jr. | WO 2010039853 A1 | 4/2010 | |
| 2005/0076906 | A1 | 4/2005 | Johnson | WO 2010059839 A2 | 5/2010 | |
| 2005/0080461 | A1 | 4/2005 | Stahmann et al. | | | |
| 2005/0081854 | A1 | 4/2005 | Nadjafizadeh et al. | OTHER PUBLICATIONS | | |
| 2005/0085738 | A1 | 4/2005 | Stahmann et al. | | | |
| 2005/0085874 | A1 * | 4/2005 | Davis et al. .................... 607/66 | | | |
| 2005/0090871 | A1 | 4/2005 | Cho et al. | | | |
| 2005/0101833 | A1 | 5/2005 | Hsu et al. | | | |
| 2005/0113646 | A1 | 5/2005 | Sotos et al. | | | |
| 2005/0113710 | A1 | 5/2005 | Stahmann et al. | | | |
| 2005/0119285 | A1 | 6/2005 | Matos et al. | | | |
| 2005/0126574 | A1 | 6/2005 | Wood | | | |
| 2005/0133026 | A1 | 6/2005 | Seleznev et al. | | | |
| 2005/0143617 | A1 | 6/2005 | Auphan | | | |
| 2005/0148893 | A1 | 7/2005 | Misczynski et al. | | | |
| 2005/0148897 | A1 | 7/2005 | Cho et al. | | | |
| 2005/0149146 | A1 | 7/2005 | Boveja et al. | | | |
| 2005/0150504 | A1 | 7/2005 | Heeke et al. | | | |
| 2005/0215947 | A1 | 9/2005 | Heruth et al. | | | |
| 2005/0240253 | A1 | 10/2005 | Tyler et al. | | | |
| 2005/0258242 | A1 | 11/2005 | Zarembo | | | |
| 2005/0277999 | A1 | 12/2005 | Strother et al. | | | |
| 2006/0095078 | A1 | 5/2006 | Tronnes | | | |
| 2006/0095088 | A1 | 5/2006 | De Ridder | | | |
| 2006/0122653 | A1 | 6/2006 | Bradley et al. | | | |

Gilliam, Edwin E. and Goldberg, Stephen J., Contractile Properties of the Tongue Muscles: Effects of Hypoglossal Nerve and Extracellular Motoneuron Stimulation in Rat, Journal of Neurophysiology, vol. 74, No. 2, Aug. 1995, pp. 547-555.

Nagai, et al., Effect of Aging on Tongue Protrusion Forces in Rats; Dysphagia (2008) 23:116-121.

Pae, Eung-Kwon et al., Short-Term Electrical Stimulation Alters Tongue Muscle Fibre Type Composition; Archives of Oral Biology, vol. 52, Issue 6 (Jun. 2007) 544-551.

Schwartz, et al., Therapeutic Electrical Stimulation of the Hypoglossal Nerve in Obstructive Sleep Apnea, Arch Otolarynogol Head Neck Surg., vol. 127, Oct. 2001, pp. 1216-1223.

Davis, et al., Development of the Bion® Microstimulator for Treatment in Obstructive Sleep Apnea, Alfred Mann Foundation, Valencia, California, Jul. 1-5, 2003, IFESS.

Sutlive et al., Whole-Muscle and Motor-Un It Contractile Properties of the Styloglossus Muscle in Rat, The American Physiological Society, 1999, pp. 584-592.

Sutlive et al., Contractile Properties of the Tongue'S Genioglossus Muscle and Motor Units in the Rat, Genioglossus Muscle Properties, Muscle & Nerve, Mar. 2000 pp. 416-425.

Smith et al., Phenotype and Contractile Properties of Mammalian Tongue Muscles Innervated by the Hypoglossal Nerve, Respiratory Physiology and Neurobiology 147 (Feb. 23, 2005) 253-262.

Sawczuk et al., Neural Control of Tongue Movement With Respect to Respiration and Swallowing, Crit Rev Oral Viol Med, 12(I):18-37 (2001).

Goding, Jr., et al., Relief of Upper Airway Obstruction With Hypoglossal Nerve Stimulation in the Canine, The Larynogscope, Feb. 1998, 108:2, pp. 162-169.

Weiss, Implications of Silicon Monolithic RFICs for Medical Instrumentation and Telemetry, IEEE, 1998 pp. 195-204.

Troyk, Injectible Electronic Identification, Monitoring, and Stimulation Systems, Annu. Rev. Biomed. Eng. 1999, 01:177-209.

Sahin et al., Closed-Loop Stimulation of Hypoglossal Nerve in a Dog Model of Upper Airway Obstruction, IEEE Transactions on Biomedical Engineering, vol. 47, No. 7, pp. 919-925, Jul. 2000.

Yoo et al., Selective Stimulation of the Hypoglossal Nerve With a Multi-Contact Cuff Electrode, 2001 IEEE, pp. 1309-1312.

Yoo et al., Selective Stimulation of the Hypoglossal Nerve: A Fine Approach to Treating Obstructive Sleep Apnea, 2002 IEEE, pp. 2049-2050.

Eisele, M.D., et al. Tongue Neuromuscular and Direct Hypoglossal Nerve Stimulation of Obstructive Sleep Apnea, Otolarynogol Clin N. Am 36 (2003) 501-510.

Tran et al., Development of Asynchronous, Intralingual Electrical Stimulation to Treat Obstructive Sleep Apena, 2003 IEEE pp. 375-378.

Huang et al., Activation Patterns of the Tongue Muscles With Selective Stimulation of the Hypoglossal Nerve, 2004 IEEE, pp. 4275-4278.

Arndt, Rewiring the Body, BusinessWeek, Mar. 7, 2005, pp. 74-82.

Yoo et al., A Neural Prosthesis for Obstructive Sleep Apnea, 2005 IEEE, pp. 5254-5256.

Wells, The Sleep Racket Who's Making Big Busks Off Your Insomnia? Forbes, Feb. 27, 2006, pp. 80-88.

International Search Report for PCT/US2007/04512 dated Nov. 29, 2007.

International Search Report for PCT/US2008/011598 dated Dec. 12, 2008.

International Search Report for PCT/US2008/011599 dated Dec. 12, 2008.

International Search Report for PCT/US2007/04514 dated Nov. 29, 2007.

Office Action dated Aug. 28, 2009 for U.S. Appl. No. 11/707,053.

International Search Report for PCT/US2009/59374 dated Dec. 3, 2009.

Office Action dated Mar. 9, 2012 for U.S. Appl. No. 12/787,206.

Final Office Action mailed Feb. 9, 2012 in connection with U.S. Appl. No. 13/097,172.

Office Action mailed Mar. 27, 2012 in connection with U.S. Appl. No. 12/681,799.

Office Action from U.S. Appl. No. 11/707,104 dated Jun. 21, 2010.

International Search Report from International Application No. PCT/US2010/036070, dated Jul. 21, 2010.

Written Opinion of the International Search Authority Application No. PCT/US2010/036070, dated Jul. 21, 2010.

Examiners Report from Australian Patent Application No. 2007217783 dated Jul. 25, 2011.

Final Office Action mailed Nov. 4, 2010 in connection with U.S. Appl. No. 11/707,104.

Non-Final Office Action mailed Nov. 5, 2010 in connection with U.S. Appl. No. 12/752,931.

* cited by examiner

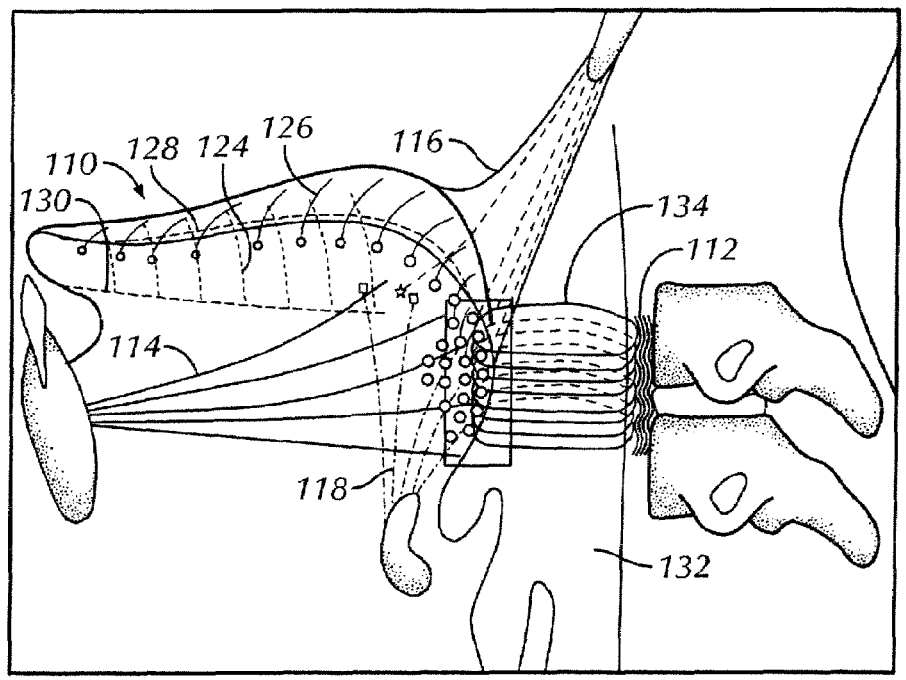
FIG. 1
*(Prior Art)*
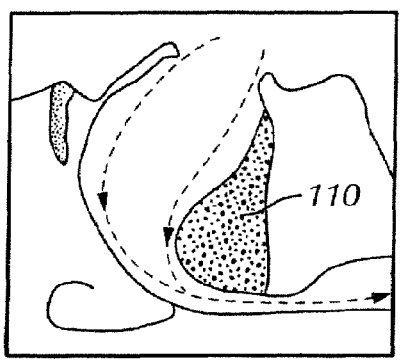 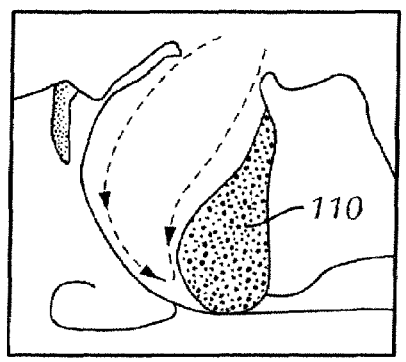
FIG. 2A　　　　　FIG. 2B
*(Prior Art)*　　　　*(Prior Art)*

METHOD OF STIMULATING A HYPOGLOSSAL NERVE FOR CONTROLLING THE POSITION OF A PATIENT'S TONGUE

CROSS-REFERENCE TO RELATED APPLICATIONS

This application claims the benefit of U.S. Provisional Patent Application No. 61/136,857 filed Oct. 9, 2008 entitled "Method of Selectively Stimulating a Hypoglossal Nerve", U.S. Provisional Patent Application No. 61/161,715 filed Mar. 19, 2009 entitled "Open Loop Stimulation of a Hypoglossal Nerve", and U.S. Provisional Patent Application No. 61/179,529 filed May 19, 2009 entitled "Open Loop Stimulation of a Hypoglossal Nerve", which are all incorporated by reference herein in their entirety.

BACKGROUND OF THE INVENTION

The present invention generally relates to a method of stimulating a Hypoglossal nerve for controlling the position of a patient's tongue. In one embodiment, the Hypoglossal nerve is stimulated to prevent obstructive sleep apnea.

Sleep apnea is a sleep disorder characterized by pauses in breathing during sleep. Those affected by sleep apnea stop breathing during sleep numerous times during the night. There are two types of sleep apnea, generally described in medical literature as central and obstructive sleep apnea. Central sleep apnea is a failure of the nervous system to produce proper signals for excitation of the muscles involved with respiration. Obstructive sleep apnea (OSA) is caused by episodes of physical obstruction of the upper airway channel (UAW) during sleep. The physical obstruction is often caused by changes in the position of the tongue 110 during sleep that results in the closure of the soft tissues 112 at the rear of the throat or pharynx 132 (See FIGS. 1 and 2A and 2B).

OSA is characterized by the complete obstruction of the airway causing breathing to cease completely (Apnea) or partially (Hypopnea). The human airway (at the level of the thorax) is lined by soft tissue, any collapse of its walls results in the closure of the airway which leads to insufficient oxygen intake, thereby interrupting one's sleep (episodes or microarousals).

During sleep, the tongue muscles relax. In this relaxed state, the tongue may lack sufficient muscle tone to prevent the tongue from changing its normal tonic shape and position. When the base of the tongue and soft tissue of the upper airway collapse, the upper airway channel is blocked, causing an apnea event (See FIG. 2B). Blockage of the upper airway prevents air from flowing into the lungs, creating a decrease in blood oxygen level, which in turn increases blood pressure and heart dilation. This causes a reflexive forced opening of the upper airway channel until normal patency is regained, followed by normal respiration until the next apneaic event. These reflexive forced openings briefly arouse the patient from sleep.

OSA is a potentially life-threatening disease that often goes undiagnosed in most patients affected by sleep apnea. The severity of sleep apnea is determined by dividing the number of episodes of apneas and hypopneas lasting ten seconds or more by the number of hours of sleep. The resulting number is called the Apnea-Hypopnea Index, or AHI. The higher the index the more serious the condition. An index between 5 and 10 is low, between 10 and 15 is mild to moderate, over 15 is moderately severe, and anything over 30 indicates severe sleep apnea.

Current treatment options range from drug intervention, non-invasive approaches, to more invasive surgical procedures. In many of these instances, patient acceptance and therapy compliance is well below desired levels, rendering the current solutions ineffective as a long-term solution.

Current treatment options for OSA have not been consistently effective for all patients. A standard method for treating OSA is Continuous Positive Airway Pressure (CPAP) treatment, which requires the patient to wear a mask through which air is blown into the nostrils and mouth to keep the airway open. Patient compliance is poor due to discomfort and side effects such as sneezing, nasal discharge, dryness, skin irritation, claustrophobia, and panic attacks. A surgical procedure where rigid inserts are implanted in the soft palate to provide structural support is a more invasive treatment for mild to moderate cases of OSA. Alternate treatments are even more invasive and drastic, including uvulopalatopharyngoplasty and tracheostomy. However, surgical or mechanical methods tend to be invasive or uncomfortable, are not always effective, and many are not tolerated by the patient.

Nerve stimulation to control the position of the tongue is a promising alternative to these forms of treatment. For example, pharyngeal dilation via Hypoglossal nerve (XII) stimulation has been shown to be an effective treatment method for OSA. The nerves are stimulated using an implanted electrode to move the tongue and open the airway during sleep. In particular, the medial XII nerve branch (i.e., in. Genioglossus), has demonstrated significant reductions in UAW airflow resistance (i.e., increased pharyngeal caliber). While electrical stimulation of nerves has been experimentally shown to remove or ameliorate certain conditions (e.g., obstructions in the UAW), current implementation methods typically require accurate detection of a condition (e.g., a muscular obstruction of the airway or chest wall expansion), selective stimulation of a muscle or nerve, and a coupling of the detection and stimulation. These systems rely on detection of breathing and/or detection of apnea events as preconditions to control and deliver electrical stimulation in order to cause only useful tongue motions and to periodically rest the tongue muscles and avoid fatigue. In one system, for example, a voltage controlled waveform source is multiplexed to two cuff electrode contacts. A bio-signal amplifier connected to the contacts controls stimulus based on breathing patterns. In another system, a microstimulator uses an implanted single-contact constant current stimulator synchronized to breathing to maintain an open airway. A third system uses an implantable pulse generator (IPG) with a single cuff electrode attached to the distal portion of the Hypoglossal nerve, with stimulation timed to breathing. This last system uses a lead attached to the chest wall to sense breathing motions by looking at "bio-impedance" of the chest wall. Still another system monitors vagus nerve electroneurograms to detect an apnea event and stimulate the Hypoglossal nerve in response.

What is needed is a system and method of electrical stimulation of the Hypoglossal nerve for controlling tongue position that is not tied to breathing and/or detection of an apnea event.

BRIEF SUMMARY OF THE INVENTION

A method of stimulating a Hypoglossal nerve for controlling the position of a patient's tongue according to some embodiments of the present invention includes attaching at least one electrode to the patient's Hypoglossal nerve and applying an electric signal through the electrode to at least one targeted motor efferent located within the Hypoglossal nerve to stimulate at least one muscle of the tongue. In one embodiment the at least one electrode is programmable.

In a further embodiment, the method includes programming a threshold amplitude and pulse duration of the electric signal by attaching the at least one programmable electrode to the patient's Hypoglossal nerve while the patient is awake and applying the electric signal to the Hypoglossal nerve at a first frequency through the at least one programmable electrode, and increasing at least one of the amplitude and pulse duration of the electric signal until one of the tongue moves and the patient reports a sensation.

In a further embodiment, the method includes programming a target amplitude and pulse duration of the electric signal by applying the threshold amplitude and pulse duration to the patient's Hypoglossal nerve at a second frequency through the at least one programmable electrode, the second frequency being faster than the first frequency, and increasing at least one of the amplitude and pulse duration of the electric signal to a target level until the tongue moves sufficiently to open the patient's airway. In a further embodiment, the method includes decreasing the second frequency to a target frequency.

In some embodiments, the at least one electrode includes at least first and second contacts and the electric signal comprises at least first and second electric signals, and the method further comprises applying the first electric signal through the first contact to a first targeted motor efferent located within the Hypoglossal nerve to stimulate at least one muscle of the tongue, and applying the second electric signal through the second contact to a second targeted motor efferent located within the Hypoglossal nerve to stimulate at least one muscle of the tongue. In one embodiment, the at least first and second contacts include a plurality of contacts forming a plurality of functional groups. In one embodiment, each functional group stimulates a different muscle. In one embodiment, each functional group includes at least one of the plurality of contacts. In one embodiment, the first and second electric signals are applied at predetermined intervals. In one embodiment, the predetermined intervals of the at least one first and second electric signals are out of phase with each other. In one embodiment, the first and second electric signals are generally equal in level and frequency. In one embodiment, the first electric signal stimulates a first muscle and the second electric signal stimulates a second muscle. In one embodiment, the first and second electric signals are applied at predetermined cycles for alternatively resting and stimulating first and second muscles. In one embodiment, the cessation of the first electric signal is coincident with the initiation of the second electric signal.

In one embodiment, the at least one targeted motor efferent is a protrusor motor efferent. In one embodiment, the at least one targeted motor efferent is a muscle that moves to improve airway patency. In one embodiment, the electric signal is applied for a predetermined duration. In one embodiment, the electric signal is automatically applied after the patient activates the electrode and following a time delay sufficient to allow the patient to fall asleep. In one embodiment, the muscle is stimulated such that one of apnea and hypopnea is prevented. In one embodiment, the electric signal is applied via an open loop system. In one embodiment, the electric signal is applied continuously for an entire sleep period.

BRIEF DESCRIPTION OF THE SEVERAL
VIEWS OF THE DRAWINGS

The foregoing summary, as well as the following detailed description of exemplary embodiments of a method of stimulating a Hypoglossal nerve for controlling a position of a patient's tongue, will be better understood when read in conjunction with the appended drawings. It should be understood, however, that the invention is not limited to the precise arrangements and instrumentalities shown.

In the drawings:

FIG. 1 is an illustration of the human airway;

FIG. 2A is an illustration of an open human airway;

FIG. 2B is an illustration of a closed human airway during an apnea event;

DETAILED DESCRIPTION OF THE INVENTION

Tongue Muscle Properties

Figure 3:
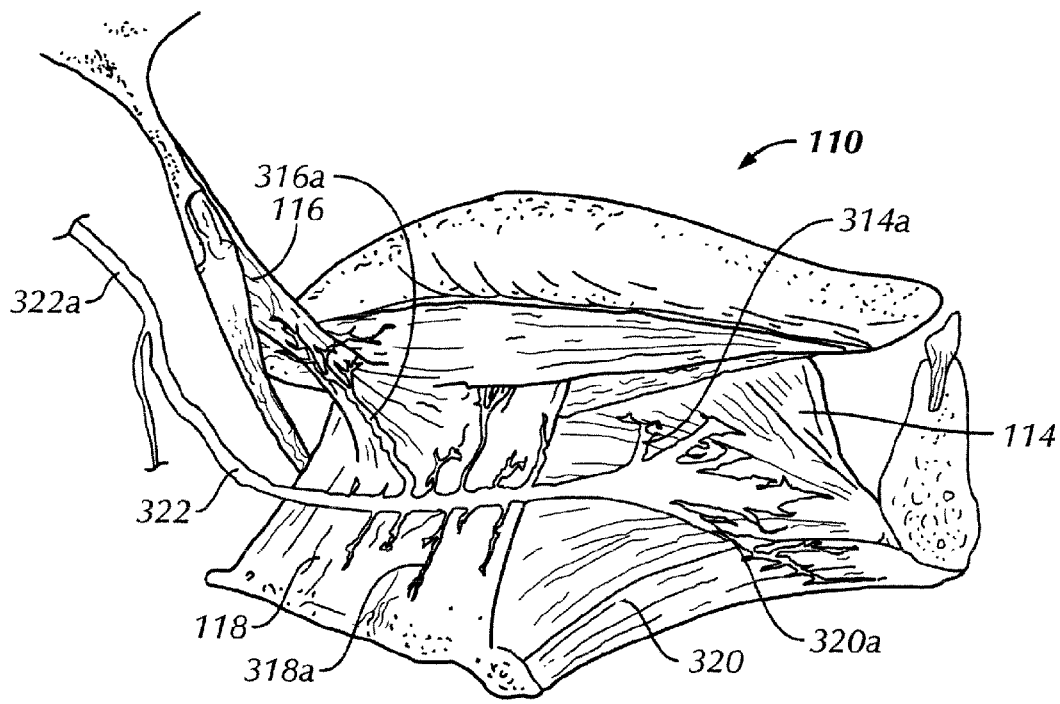
FIG. 3 is an illustration of the human tongue.

Referring to FIGS. 1 and 3, the tongue 110 has been described as a hydrostat—a specialized muscle able to move and change shape without the usual tendon connections to bones against which forces may be applied. Much like the trunk of an elephant, the tongue 110 can change shape and move within the oral cavity to aid in speaking, eating, and breathing. The tongue muscles include the Genioglossus muscle 114, the Styloglossus muscle 116, the Hyoglossus muscle 118, the Palatoglossus muscle (not shown), the Geniohyoid muscle 320 (the Geniohyoid muscle 320 is not a tongue muscle but it is an important protrusor and pharyngeal dilator) and several muscles that lie within the tongue, called the intrinsics. In a patient who is awake, the brain supplies neural drive to these muscles through the Hypoglossal nerve 322, to move the tongue 110 and to change its shape. The Hypoglossal nerve 322 includes a Styloglossus branch 316a, Hyoglossus branches 318a, Genioglossus branches 314a, and Geniohyoid branches 320a. In a patient who is awake, the neural drive to the tongue muscles act to maintain tongue shape and position, preventing the tongue 110 from blocking the airway.

The tongue 110 comprises both intrinsic and extrinsic lingual muscles. There are four intrinsic—i.e., origin and insertion within the tongue 110—lingual muscles: Verticalis 124, Transversalis 126, Superior Longitudinalis 128, and Inferior Longitudinalis 130. There are four extrinsic—i.e., external bony origin and insertion in to the tongue base—lingual muscles (mentioned above): Genioglossus 114, Styloglossus 116, Hyoglossus 118, and Palatoglossus. The lingual muscles are also functionally categorized as either retrusor or protrusor muscles and both intrinsic and extrinsic muscles fall into these category. The retrusor lingual muscles include the intrinsic Superior and Inferior Longitudinalis muscles 128, 130 and the extrinsic Hyoglossus muscle 118 and Styloglossus muscle 116. The protrusor lingual muscles include the intrinsic Verticalis and Transversalis muscles 124, 126 and the extrinsic Genioglossus muscle 114. The elevation of the tongue 110 is achieved by the contraction of the Styloglossus muscle 116 while the depression is the result of downward movements of Hyoglossus and Genioglossus muscles 118, 320.

Hypoglossal Nerve Efferents

Figure 4:
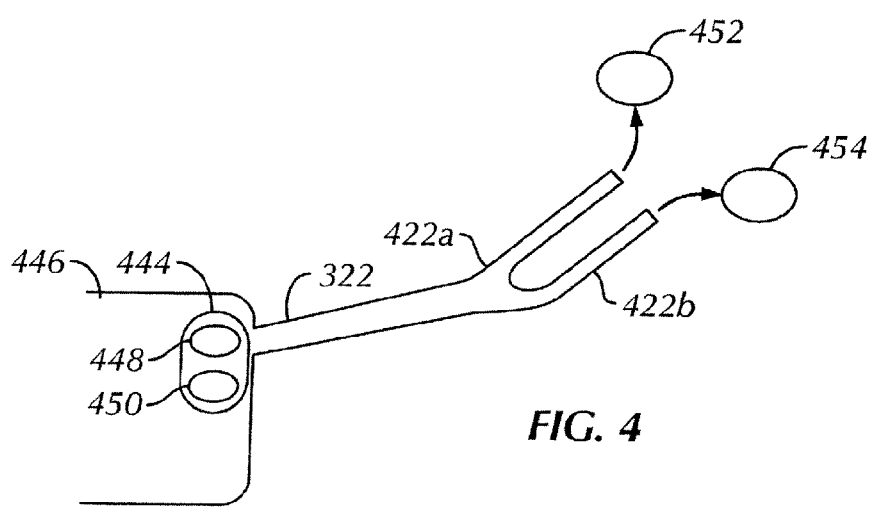
FIG. 4 is a schematic illustration of the motor nerve organization of the Hypoglossal nerve.

FIG. 4 schematically illustrates the motor nerve organization of the Hypoglossal nerve 322 from its origin in the motor nuclei 444 in the Hindbrain 446—specifically the location of the retrusor and protrusor cell bodies 448, 450—extending via their axons to the retrusor muscle 452 and protrusor muscle 454 innervated by the lateral 422a and medial 422b branches, respectively of the Hypoglossal nerve 322.

Figure 5:
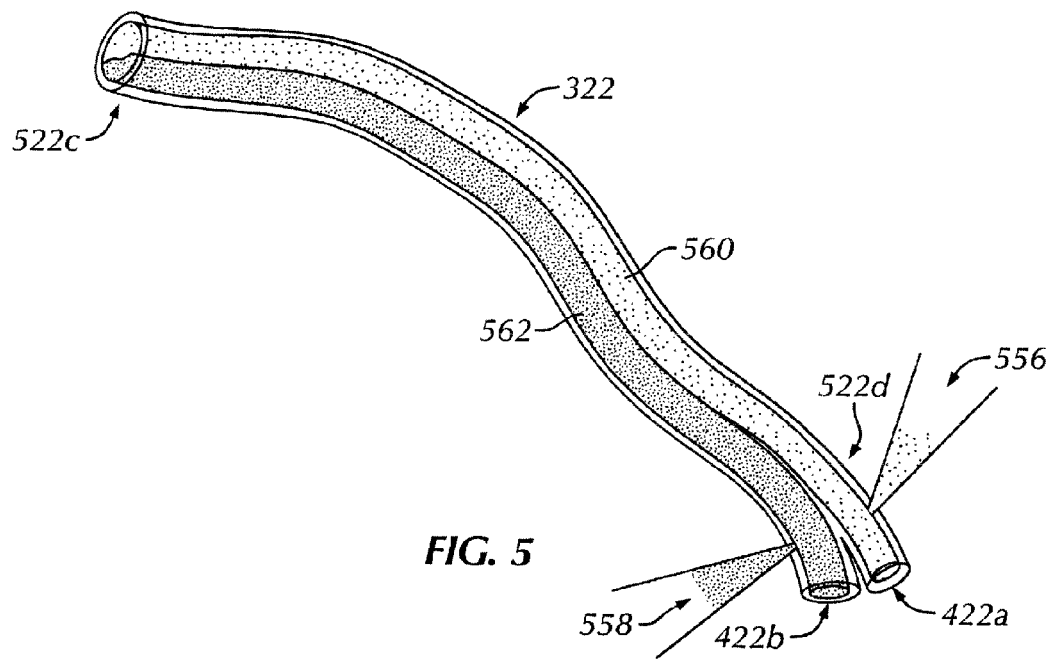
FIG. 5 is an illustration of the Hypoglossal nerve shown in FIG. 4 with labeling of the lateral and medial branch nerve fibers.
Figure 6:
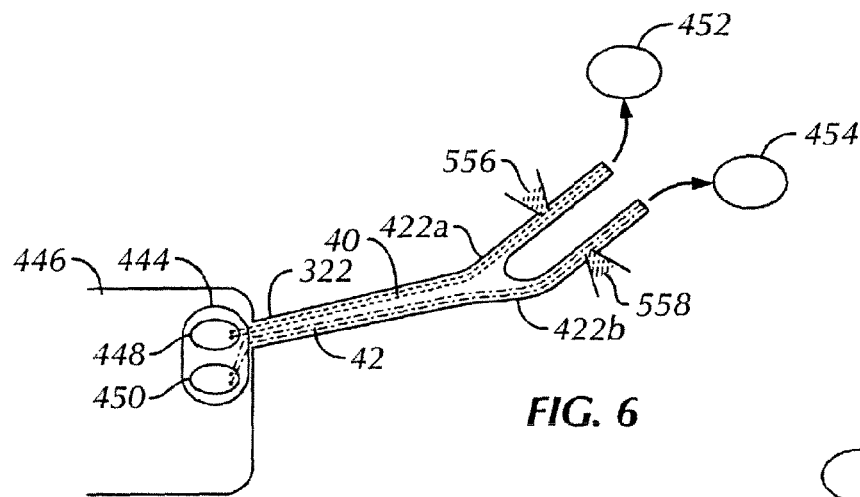
FIG. 6 is a schematic illustration of the Hypoglossal nerve shown in FIG. 4 with labeling of the lateral and medial branch nerve fibers.
Figure 7:
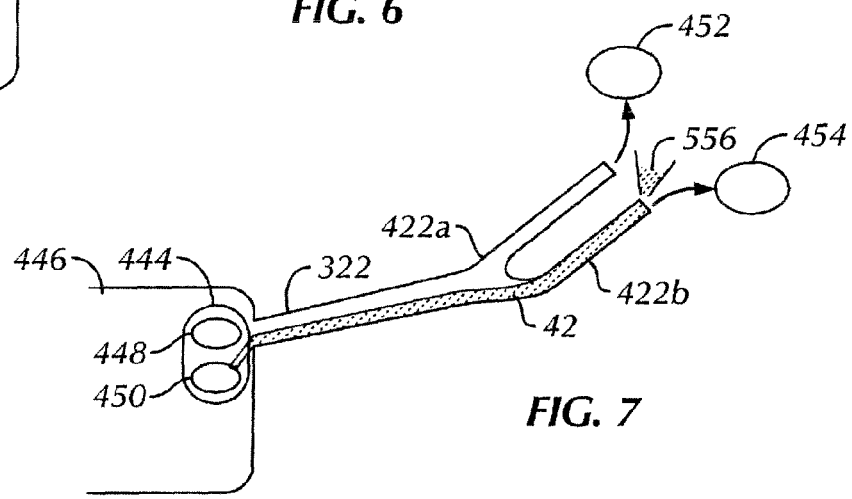
FIG. 7 is a schematic illustration of the Hypoglossal nerve shown in FIG. 4 with labeling of the medial branch nerve fibers.

Referring to exemplary FIGS. 5-7, the present invention's novel method of mapping Hypoglossal nerve efferents was demonstrated in a rat using dyes DiI 556 (for example, 1,1'-dioleyl-3,3,3',3'-tetramethylindocarbocyanine methanesulfonate) and DiO 558 (for example, 3,3'-dilinoleyloxacarbocyanine perchlorate). In one embodiment, the fluorescent dyes are manufactured by Molecular Probes. The use of the dyes DiI 556 and DiO 558 disclosed a surprising and unexpected anatomical and topographical organization of the Hypoglossal nerve 322. This anatomical and topographical organization permits targeted stimulation of portions of the Hypoglossal nerve 322 to maximize the efficacy of the stimulation as described further below.

In a first experiment, efferents of the medial and lateral branches 422a, 422b were micro-injected with dyes DiI 556 and DiO 558, respectively. Nerve branches were exposed and the tips of dye-loaded capillaries were pierced through the perineurium of each branch 422a, 422b. The dye solution was iontophoresed using a current source (Kation Scientific, Minneapolis, USA) at 4 µA for five seconds on and five seconds off duty cycle for five minutes.

In a second experiment, the Medial branch 422b and protrusor musculature were surgically exposed and injected with DiI 556. The tips of dye-loaded capillaries were pierced into the muscle bellies of selected protrusor muscles 454 and their innervating branches. The dye solution was iontophoresed using a current source (Kation Scientific, Minneapolis, USA) at 4 µA for five seconds on and five seconds off duty cycle for five minutes.

Figure 5B:
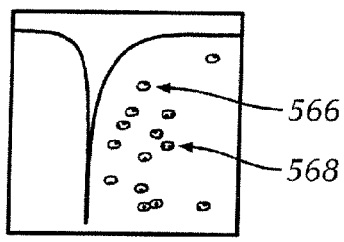
FIG. 5B is an illustration of the motor neurons in the Hindbrain.

FIGS. 5 and 6 schematically show the effects of injecting the dyes Da 556 and DiO 558 into the lateral and medial branches 422a, 422b, respectively, of the Hypoglossal nerve 322. The dye DiI 556 injected into the lateral branch 422a of the Hypoglossal nerve 322 remains confined to the Hypoglossal nerve efferents located within the lateral branch 422a and spreads rostrally towards the retrusor muscles 452 and anteriorly towards the location of the retrusor cell bodies 448 in the motor nuclei 444 in the hindbrain 446. The dye DiO 558 injected into the medial branch 422b of the Hypoglossal nerve 322 remains confined to the Hypoglossal nerve efferents located within the medial branch 422b and spreads rostrally towards the protrusor muscles 454 and anteriorly towards the location of the protrusor cell bodies 450 in the motor nuclei 444 in the brain 446. FIG. 5B illustrates the DiO and DiI labeled neurons 556, 568.

Figure 5A:
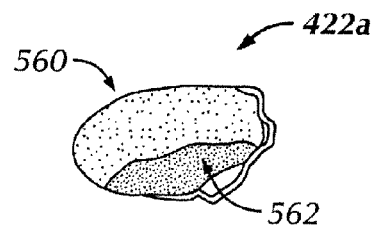
FIG. 5A is a cross sectional illustration of the Hypoglossal nerve shown in FIG. 5.

Referring to FIG. 5A, the magnified section of the lateral branch 422a of the Hypoglossal nerve 22 demonstrated that it is almost exclusively comprised of the DiI illuminated retrusor motor efferents 560. Similarly, a magnified section of the medial branch 422b of the Hypoglossal nerve 322 (not shown) demonstrated that is almost exclusively comprised of the DiO illuminated protrusor motor efferents 562. Consistent near segregation was found of the retrusor motor efferents dorsolaterally and the protrusor motor efferents ventromedially.

This anatomical and topographical compartmentalization was confirmed via a modified labeling protocol. FIG. 7 illustrates that dye DiI 556 may be injected into either the terminal end of the medial branch 322b or into the protrusor musculature 454 and the dye DiI 556 will travel anteriorly and ventromedially through the Hypoglossal nerve proper 322. A confocal fluorescent image of the entire Hypoglossal nerve 322 demonstrated the consistent ventromedial localization of the DiI labeled protrusor motor efferents 560 from the medial branch 422b through the Hypoglossal nerve proper 322 to the brain 446 and high magnification confocal images of the DiI labeled axons.

Figure 8A:
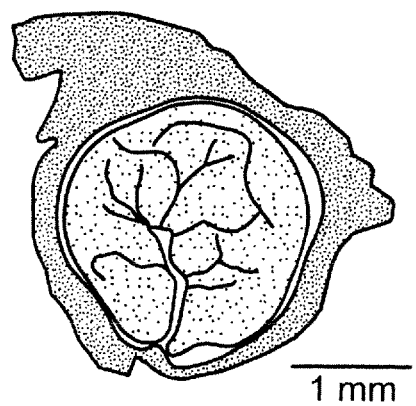
FIG. 8A is an illustration of a cross-section of a human Hypoglossal nerve.
Figure 8B:
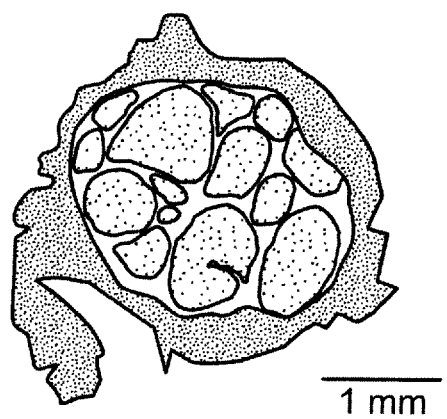
FIG. 8B is an illustration of a cross-section of a human Lingual nerve.
Figure 8C:
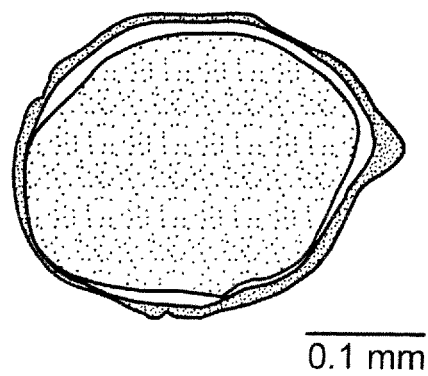
FIG. 8C is an illustration of a cross-section of a rat Hypoglossal nerve.

FIGS. 8A, 8B and 8C demonstrate the organization structure of the Human Hypoglossal nerve (FIG. 8A) and the Human Lingual Nerve (FIG. 8B), as well as the Rat Hypoglossal Nerve (FIG. 8C). The Hypoglossal nerves in both Human and Rat are afascicular, lacking the clear organizational structure present in most peripheral nerves, and which is present in the Human Lingual Nerve.

It is believed that the non-fascicular structure of the Hypoglossal nerve in rats approximates the structure of the Hypoglossal in humans. Moreover, the over-all musculature (organization of extrinsic and intrinsic muscles) in the rat tongue and the human tongue, is nearly identical. U.S. Provisional Patent Application No. 61/136,857 filed Oct. 9, 2008 entitled "Method of Selectively Stimulating a Hypoglossal Nerve", which has been incorporated by reference in its entirety, discusses and illustrates the similarities between the rat and human tongues in further detail.

It has therefore been demonstrated that the surprising and unexpected anatomical and topographical compartmentalization forms the basis of the present invention which relates to a method of treating, controlling, or preventing a neurological disorder using selective targeted electrical nerve stimulation of the Hypoglossal nerve proper 22, and more particularly to a method of selective electrical stimulation of motor efferents (e.g., retrusor and protrusor motor efferents) of the Hypoglossal nerve 322. The words "selective" and "targeted" are used interchangeably herein meaning the use of electrodes and current sources to selectively activate targeted nerve fibers within a nerve bundle and hence their associated motor groups to achieve a specific motor function. In the case of obstructive sleep apnea, electrical stimulation of efferents of the Hypoglossal nerve 322, and more specifically, targeted stimulation of the protrusor motor efferents located in Hypoglossal nerve proper 322 and/or the medial branch 422b, for example, can open up the airway and maintain the patency of the upper airway channel.

The above described surprising anatomical and topographical organization may help to explain some of the failures and limitations of previous Hypoglossal nerve stimulation applications. Specifically, electrical stimulation of the whole Hypoglossal nerve proper 322—i.e., the section of the Hypoglossal nerve 322 located proximal to its bifurcation into the medial and lateral branches 422a, 422b—resulted in combined (non-specific) contractions of both intrinsic and extrinsic muscles and both retrusor and protrusor muscles 452, 454. As both the retrusor and protrusor muscles 452, 454 comprise intrinsic and extrinsic muscles, electrical stimulation of either the medial or lateral branches 422a, 422b alone results in recruitment of both intrinsic and extrinsic muscles. Further, stimulation of the Hypoglossal nerve proper 322 may excite sensory afferent and motor efferent fiber types. Grossly, the fused contractions of this non-selective stimulation results not only in undesirable sensory stimulation but also presents as a slight ipsilateral deviation and retrusion of the tongue 110.

Known stimulation of the Hypoglossal nerve proper has also resulted in cases of profound bradycardia which is believed to be related to secondary vagus nerve stimulation: the Hypoglossal nerve lies against the posterior surface of the vagus and superior cervical sympathetic ganglion where it exchanges branches of communication, and is united with the inferior vagal ganglion of the vagus by connective tissue. Common forms of electrical stimulation elicit action potentials in the nerve axon that propagate in two directions: towards the desired muscle or end organ, and in the antidromic direction towards the cell body, the same direction that sensory fibers would normally transfer their information. It is possible that this antidromic activity could be eliciting the secondary vagus nerve activation. A more distal site of stimulation—e.g., the medial branch 22b—may avoid unwanted vagal nerve reflex and muscle activation because of its more limited neural connections, but will still non-selectively recruit both sensory afferent and motor efferent fiber types if they both exist within the range of the stimulating electrode. By discerning the extent and myotopic organization of the Hypoglossal nerve motor neuron subgroups and the muscles(s) thereby innervated, such knowledge can be used to specify the functional relevance of diverging efferent systems and in elucidating mechanisms underlying tongue control. Accordingly, in one embodiment, the present invention is directed to a method of mapping Hypoglossal nerve fibers, thereby allowing the claimed method of selective recruitment of specific nerve fibers, as well as methods for selective stimulation. Understanding the neural organization allows for selective targeted stimulation that activates only those muscle groups that are desirable, and avoids activating those which are not. The knowledge gained from animal and cadaver studies validate the methods of selective stimulation described herein. The process of using selective stimulation allows for the selective activation of only the desired muscle functions.

It should be noted, additionally, that activation of a small fraction of retrusor muscle or muscles along with the activation of protrusor muscles can act to reduce pharyngeal compliance while not significantly leading to tongue retrusion, and may have a beneficial effect in airway patency.

Apparatus for Stimulation of Hypoglossal Nerve Efferents

Figure 10:
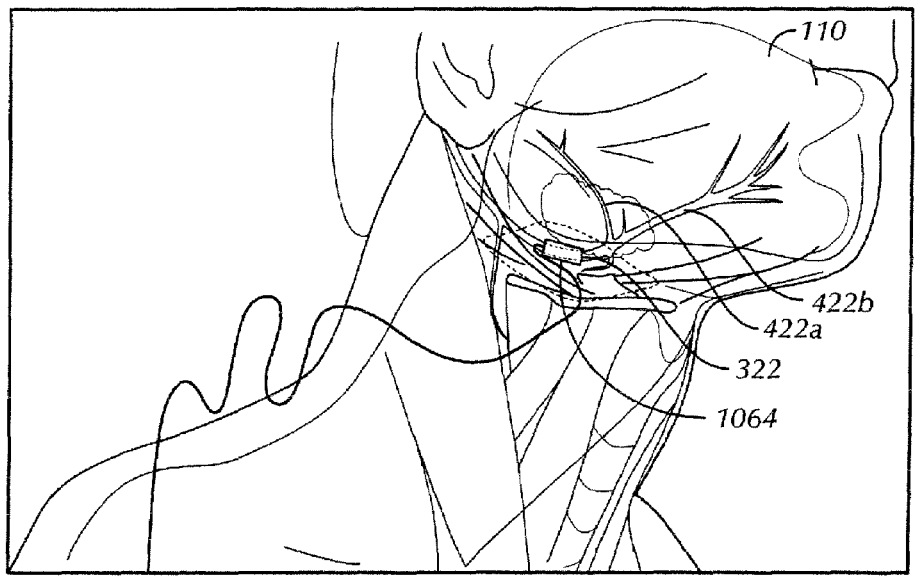
FIG. 10 is an exemplary illustration of an electrode attached to a patient's Hypoglossal nerve.
Figure 11:
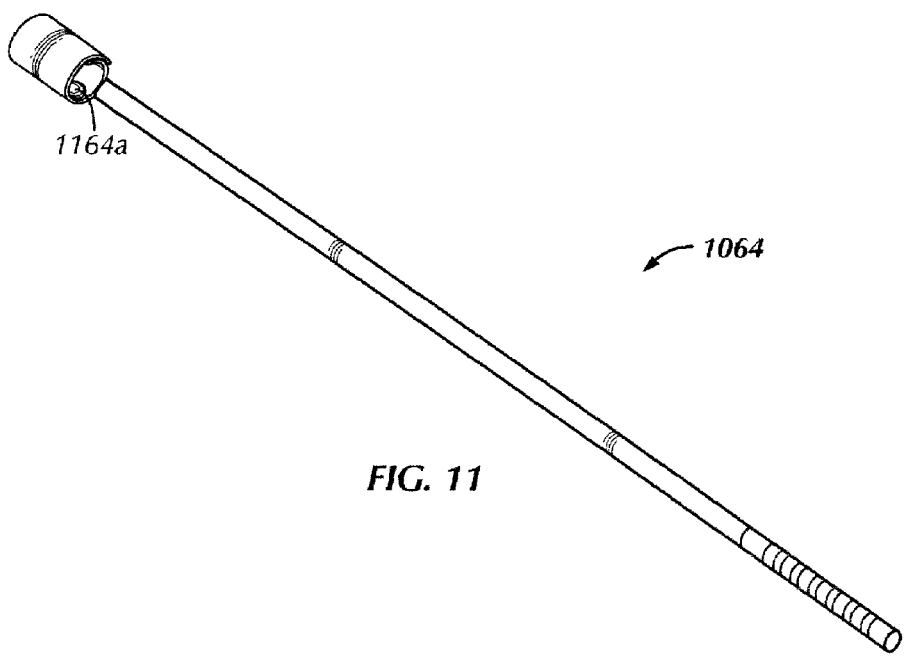
FIG. 11 is a perspective view of the electrode shown in FIG. 10.
Figure 12:
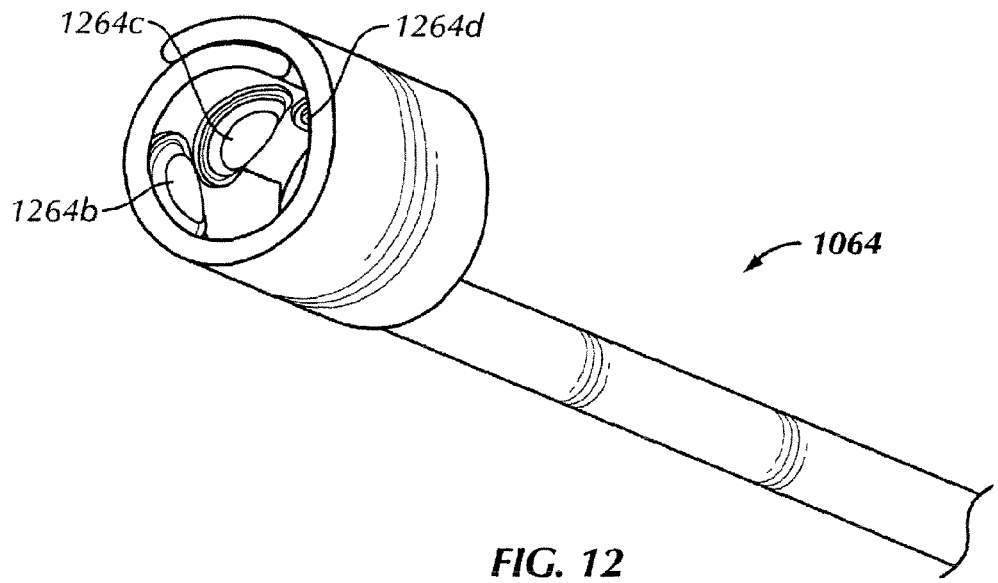
FIG. 12 is a perspective view of the electrode shown in FIG. 11 showing the plurality of contacts.

Referring to FIGS. 10-12, in one embodiment, an electrode 1064 is attached to the Hypoglossal nerve to apply at least one electric signal to a first targeted motor efferent located within the Hypoglossal nerve 322. The electrode 1064 may be programmable. The electrode 1064 may include a plurality of contacts (e.g. contacts 1164a, 1264b, 1264c, 1264d) each applying an electric signal to a targeted motor efferent. In one embodiment, each contact applies an electric signal to a different targeted motor efferent. In one embodiment, more than one contact applies an electric signal to a single targeted motor efferent. In one embodiment, the electrode 1064 includes a first contact (e.g. contact 1164a) to apply a first electric signal to a first targeted motor efferent, a second contact (e.g. contact 1264b) to apply a second electric signal to a second targeted motor efferent, a third contact (e.g. contact 1264c) to apply a third electric signal to a third targeted motor efferent and a fourth contact (e.g. contact 1264d) to apply a fourth electric signal to a fourth targeted motor efferent. In one embodiment, the targeted motor efferents that are stimulated stimulate at least one muscle of the tongue 110 to control the position of the tongue 110. In one embodiment, the electrode 1064 is a biocompatible, soft material cuff electrode that provides an intimate connection to the nerve. In another embodiment, a lead wire connects the programmable electrode to the control system. In one embodiment, the apparatus does not require a lead wire connecting the programmable electrode to the control system. In one embodiment, the control system includes a battery, either primary or rechargeable, for powering the apparatus. In one embodiment, the control system includes a processor for setting up stimulation parameters to achieve the desired outcome for the individual patient or otherwise controlling the stimulation. In one embodiment, stimulation parameters are selected from the group consisting of, but not limited to, stimulation amplitude, stimulation frequency and stimulation duration. In one embodiment, the control system includes a mechanism that allows the patient to turn the apparatus on and off and possibly make adjustments within preprogrammed settings.

The method provided by the present invention is not limited by the design of the apparatus used to carry it out except to the extent the point of contact with the Hypoglossal nerve proper 322 or its lateral and medial branches 422a, 422b is consistent with the teachings herein. Although an exemplary apparatus for selectively stimulating Hypoglossal nerve efferents is shown, equivalent alterations and modifications will occur to others skilled in the art upon reading and understanding this specification and annexed drawings. For example, U.S. Patent Publication No. 2008/0046055, WO 2009/048580 and WO 2009/048581, the contents of which are incorporated herein by reference in their entirety, can be modified in accordance with the teachings herein for stimulating the Hypoglossal nerve 322. In particular regard to the various functions performed by the herein described exemplary apparatus, the terms used to describe the exemplary apparatus are intended to correspond to any apparatus that is functionally equivalent—i.e., even though not structurally equivalent, that performs the function in the herein illustrated exemplary apparatus of the present invention. For further information regarding an apparatus which may be modified in accordance to the teachings herein for practicing the method of the present invention, refer to U.S. Pat. Nos. 6,456,866 and 6,587,725, which are hereby incorporated herein by reference in their entirety.

Fatigue

Figure 9:
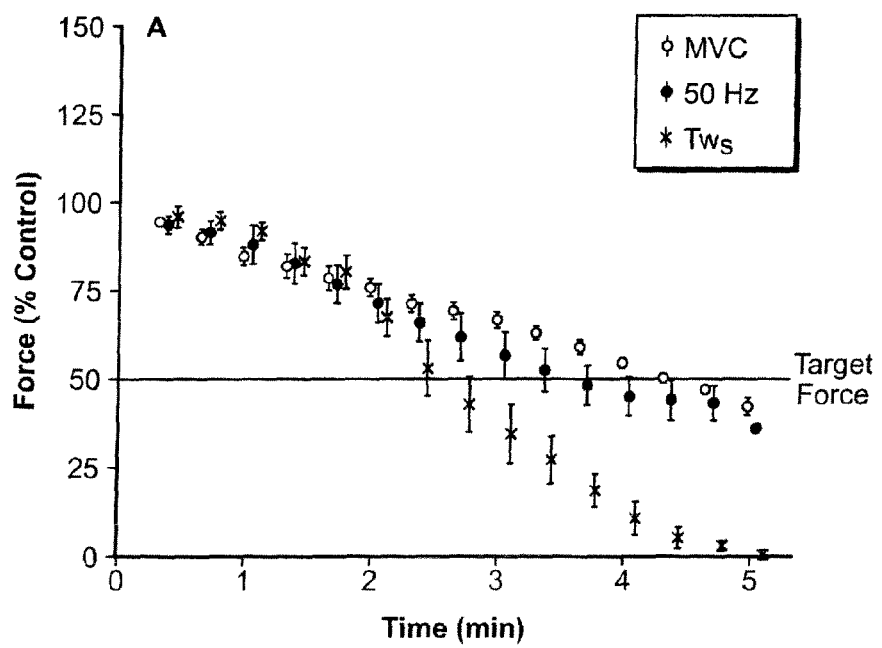
FIG. 9 is an exemplary set of fatigue curves of human quadriceps muscle showing maximum voluntary contraction, 50 Hz electrical stimulation and twitch responses.

FIG. 9 illustrates an exemplary fatigue curve. Fatigue is a common phenomenon with artificial activation by electrical stimulation of a muscle. In voluntary muscle control, the human brain recognizes, organizes, and selects the best muscle fibers to activate for a particular activity. It brings fibers in and out of activation to minimize or prevent fatigue and maintain muscle output. In artificial activation by electrical stimulation however, stimulation comes from one or more electrode contacts located in a relatively fixed position with respect to a targeted nerve or nerve fiber bundle. The same population of fibers are activated essentially every time that a stimulus is applied because of this fixed relationship.

Figure 15:
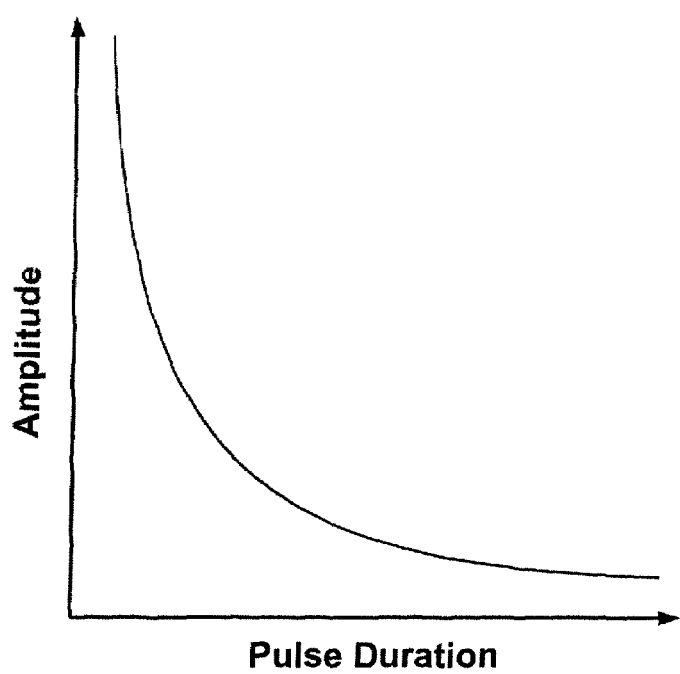
FIG. 15 is an exemplary strength-duration curve.

As is known in the art, excitation of a nerve fiber can occur along a strength duration iso-threshold curve—a nerve fiber will be excited as long as the amplitude is above the curve or the phase duration is to the right of the curve. An exemplary strength curve is shown in FIG. 15. At either end of the curve the shape of the curve is asymptotic—at a limiting phase duration no amount of stimulation current elicits a response, and at the other no phase duration is long enough to elicit a response either. The invention described here refers to the use of stimulus amplitude for means of modulating the recruitment of nerve fibers, but it shall be understood that many methods, including phase duration and stimulus amplitude, can be utilized to the same ends of activating nerve fibers with electrical stimulation.

Nerve fibers are preferentially activated, or recruited, in the order of their proximity to the electrode contact and by their fiber diameter. As a general rule, the closer a fiber is to the cathodic contact, the more likely it will be activated (the general form of a stimulating system is to place the cathodal contact in close proximity to the target nerve axons; other forms of stimulation exist and shall be obvious to those skilled in the art). The larger the diameter of a fiber, the more likely it will be activated. The distance and size distribution in a nerve bundle does not change appreciably over time. Hence, the recruitment properties—which fibers will be activated with a particular amplitude pulse—do not change either. If the applied stimulus is maintained at a sufficiently high enough frequency, the recruited muscle fibers activated by the stimulated nerve fibers eventually fatigue. Muscle force and/or position then change to the relaxed, inactivated condition. The stimulation of skeletal muscle for postural control or limb motion is often performed at frequencies that would normally be expected to cause fatigue in those muscles along with the loss of desired function if the stimulation were maintained continuously. Stimulation may be modulated by changing the stimulus amplitude, as described above, or by changing the phase duration of the pulse. Great care and tremendous effort are expended in avoidance of fatigue in skeletal muscle applications for fear of loss of desired functional effect, for example, for patients suffering from spinal cord injury or other neurological dysfunction.

Fatigue may be minimized or prevented by using a stimulation duty cycle—that is, stimulating for a certain amount of time before significant fatigue sets in, then stopping to let the muscle rest and regain its ability to contract. For obstructive sleep apnea this is less than optimal because without an applied stimulus during the off period of the electrical stimulation duty cycle the tongue would not be driven to maintain a desired position, and could fall back against the rear of the throat and allow an apnea event to occur. This is one of the reasons that many OSA stimulation systems rely on sensors to detect when to apply stimulation and when to leave it off. The method of using duty cycle to rhythmically apply stimulation has been proposed, also, to do away with the need to sense breathing events, in the hopes that by introducing rhythmic stimulation to the Hypoglossal nerve that somehow the breathing events would synchronize automatically to the stimulation timing. This has not been proven and the study by Davis, et al, using microstimulators in sheep demonstrated that manual timing of stimulation to the events of breathing was required to achieve a useful outcome in single point stimulation of the Hypoglossal nerve.

Another method of minimizing or preventing fatigue is to use one or more independent current sources to activate multiple portions of the desired muscle groups. In certain exemplary embodiments, one or more independent current sources drive one or more contacts (1164*a*, 1264*b*, 1264*c* and 1264*d* for example shown in FIGS. 11 and 12) that interface with the Hypoglossal nerve 322. These contacts are optionally contained in a single cuff electrode 1064 as shown. Each contact can be activated separately or in combination with other contacts.

Figure 13:
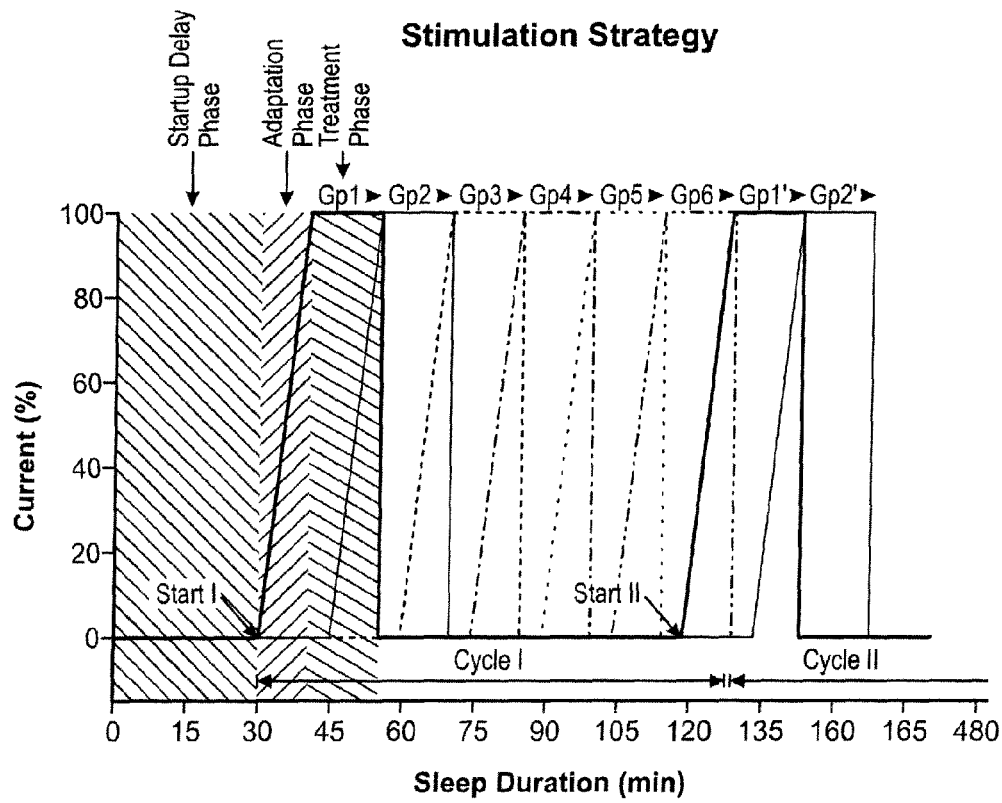
FIG. 13 is a graphical representation of an exemplary stimulation strategy.

In certain embodiments, each contact is assigned to one or more functional groups. Functional groups may in turn be used to select regions of fibers within the nerve bundle that result in a desired tongue movement. The effort of moving the tongue to the desired position is thus shifted from one functional group to another functional group so that no single functional group is required to work all of the time. Thus, the effort of moving the tongue is shared among multiple stimulated nerve fibers and their associated muscles, preventing or reducing fatigue because none of the groups is activated long enough to cause significant fatigue, and during their off state they are allowed to recover from the stimulation. In certain exemplary embodiments, each group is active until just before significant fatigue sets in. One or more other groups are then activated to take its place, allowing the former muscle group fibers to rest. In one embodiment, the stimulation is spread over more than one contact wherein the duty cycle of each contact is overlapped (FIG. 13). In one embodiment, the stimulation pulses may be generally random or pseudo random so long as the overall contractions per unit of time is limited (see FIG. 14D).

Figure 14A:
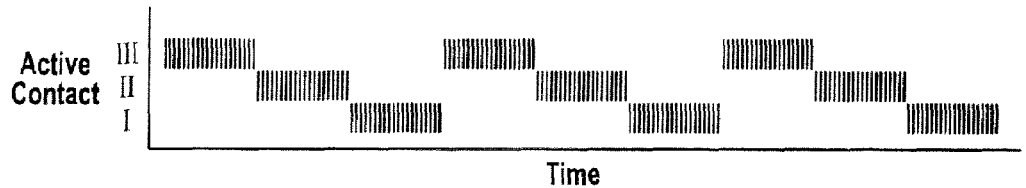
FIG. 14A is a graphical representation of an exemplary duty cycle stimulation strategy.
Figure 14B:
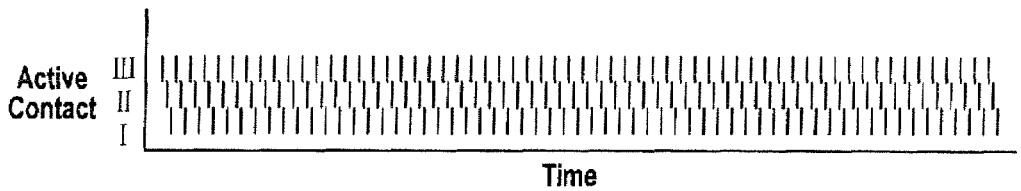
FIG. 14B is a graphical representation of an exemplary interleaved stimulation strategy.
Figure 14C:
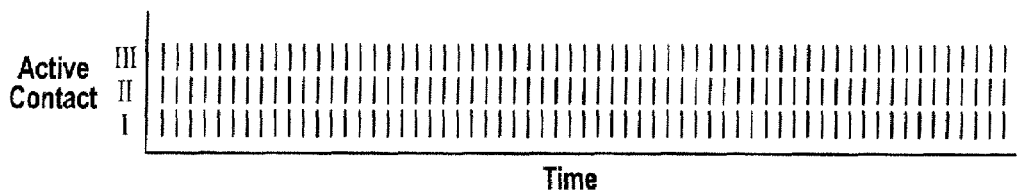
FIG. 14C is a graphical representation of an exemplary synchronous stimulation strategy.
Figure 14D:
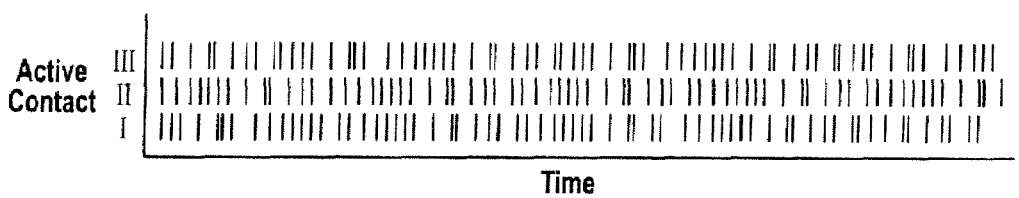
FIG. 14D is a graphical representation of an exemplary asynchronous or random stimulation strategy.

Another method of reducing or eliminating fatigue is to lower the stimulation frequency. The faster a nerve is stimulated, the faster it fatigues. Each pulse produces a contraction, with each contraction requiring a certain amount of work. The more contractions there are, the more the muscle works, and the more likely the muscle will become fatigued. Reducing the stimulation frequency to a rate just fast enough to achieve the desired response minimizes the rate at which muscle contractions occur. This minimizes the amount of work done by the muscle, delaying or minimizing muscle fatigue. In one embodiment, the stimulation is spread over more than one contact wherein each contact delivers a generally equal fraction of stimulation frequency that is out of phase with the other contacts (FIG. 14B). This method reduces the stimulation rate for each of the independent groups but results in a functional stimulation rate that is essentially the sum of the rates that are active. As shown in FIGS. 14A and 14B, the same effective force or position is maintained, but in FIG. 12A fatigue is prevented by duty cycle method and in FIG. 14B it is prevented by three groups running at one third the frequency of any one group in FIG. 14A, resulting in the same muscle force or position and the same prevention of fatigue. Stimulation frequencies that have been used for activating skeletal muscle have often required the use of a frequency that results in tetanus, a smooth fusion of pulses fast enough to maintain a near continuous level of force or position. Tetanus is not required, per se, in the artificial activation of the tongue—the patient is asleep, and the cosmetic appearance of the tongue while it is activated is not nearly as important as the maintenance of airway patency. Experimental evidence has shown that stimulating at frequencies below 5 pulses per second have been adequate to maintain airway patency in patients with severe OSA.

Continuous or near continuous stimulation of a muscle is discouraged in the art because of fatigue problems. However, in view of the teaching herein, the tongue 110 is a fatigue resistant muscle. Testing in both rats and humans has confirmed this finding. In limited animal studies, it was demonstrated that rat tongue muscle could be stimulated at very high frequencies for extended periods without observable changes in tongue position. In one study, rather than stimulating at 15 pulses per second (pps), a frequency adequate to move the tongue sufficiently to clear the rear of the throat, stimulation was applied at supra-threshold levels at a frequency of 100 pps. The resulting tongue response was maintained for more than one hour before any significant change in tongue position could be detected. If the stimulation frequency were dropped to 15 pps, it is likely that stimulation may be applied more than five times longer before tongue position change would be expected to occur. In human trials, embodiments disclosed herein successfully stimulated patients with a fixed set of electrode contacts for many hours before the anti-apnea effect was seen to diminish. In one embodiment, using lower frequencies and multiple contacts on a human tongue increases the duration that stimulation could be applied before anti-apnea effects diminish.

Preventing OSA by Open Loop Stimulation

Certain exemplary methods address this problem by applying constant, or near-constant electrical stimulation to the Hypoglossal nerve. The stimulation maintains a sufficient muscle tone by applying an artificial neural drive to the Hypoglossal nerve fibers that preferentially move the tongue to a position that clears the airway. In certain exemplary embodiments, open loop stimulation is used. The open loop stimulation in these embodiments achieves a physical response previously obtained using surgical procedures to make a long-term static change in the airway geometry during its employment.

The presence or absence of tone is also associated with the mechanism of the stiffening of the airway walls, thereby making them less compliant or less easily collapsible. Half of the retroglossal airway is lined by the back of the tongue while the other half is made up of mid-pharyngeal wall. There is a close anatomical and functional relationship between the Tranversalis muscles (intrinsic lingual) and Superior Pharyngeal constrictor muscles 134 at the base of the posterior tongue (Seiji Niimi et. al., *Clinical Anatomy*, Volume 17 (2), page 93). These two muscles complement each other in maintaining the airway shape. Movement of the lingual muscles (protrusion or retrusion) not only results in the stiffening of the wall of the posterior tongue but also stretches and stiffens (imparts an indirect drag via Superior Pharyngeal constrictor muscles) the other parts of the pharyngeal wall, making it less compliant and thus causing beneficial airway changes that effect air flow.

Thus, with the tongue and associated rear throat tissues consistently driven in such a manner as to clear the airway there is no need to detect apneas because they simply will not be allowed to occur. Rather than timing stimulation to breathing, or monitoring for an apnea event prior to initiating treatment, the exemplary embodiments stimulate the Hypoglossal nerve in a predetermined manner via an open loop system to activate targeted muscles in the tongue to maintain airway patency. With airway resistance decreased and/or the tongue prevented from falling back against the rear of the throat, anchor pharyngeal compliance reduced, there is no need to monitor for apneas, because they are prevented from occurring, nor monitor for ventilation timing because the stimulation is not timed or synchronized to breathing at all, it is maintained continuously during the entire sleeping period.

The activation of a protrusor that moves the tongue forward and away from the oral-pharyngeal junction, or the activation of a retrusor that acts to decrease the compliance of the pharyngeal wall are both desirable in preventing the occlusion of the airway. The activation of intrinsic muscles that change the shape of the tongue may also lead to desirable motions even though the actions of these muscles may not be clearly defined in terms of protrusor or retrusor. It shall be understood that the activation of any tongue muscle that achieves beneficial motions or actions of the tongue musculature is a potential target of the selective targeted methods of electrical stimulation as described by the methods of this patent and it shall not be the single object of the described method to only activate protrusors per se.

Since the tongue is a fatigue-resistant muscle, it can be stimulated, using the techniques described herein, for long durations without loss of force or movement. By stimulating the Hypoglossal nerve, tongue activation resembling normal daytime tongue muscle tone is restored to key muscles during sleep. The tongue does not fall into the throat, keeping the airway open and allowing the patient to breathe normally during sleep. Continuous or near-continuous stimulation maintains the tongue in a desired position, shaping the airway, without the necessity of a complicated closed loop stimulation strategy with the associated dependence upon sensors and their interpretation. While the tongue musculature is fatigue resistant, it is still susceptible to fatigue in general. Therefore methods employed herein are still directed at maintaining therapeutic effect by utilization of multiple groups to maintain desired function and other methods such as frequency control to minimize the work load of any single muscle group.

Problems with Detecting Changes in Respiration

It is difficult to detect an event or a change in respiration and use information such as polysomnography data prior, during and after an apnea event, to control delivery of stimulation in an implanted system. With open loop stimulation, stimulation is not timed to breathing activity, nor is stimulation tied to detecting apnea activity. Detection of changes in respiration requires the use of sensors, electronic circuitry to condition the signals received from the sensors, and processing algorithms to analyze the data and make decisions about the data recorded. Sensing often cannot occur directly but by inference from other signals. Impedance plethysmography depends upon the fact that when the chest wall expands with an inspiration that the impedance across the chest changes accordingly. Pressure sensors monitoring thoracic pressures likewise infer breathing activity by correlating pressure to changes in the breathing cycle. Monitoring the electroneurogram of the vagal or Hypoglossal nerve to either detect breathing events or apneaic events is likewise extremely difficult. All of these sensors are subject to noise or disturbance from other sources making the clear distinction of events more difficult to detect or worse, causing the false detection of an event. The addition of sensors to an implanted system increases the complexity of the leads and header assembly of an implanted pulse generator and controller and increases the likelihood for the opportunity for system failure and makes the surgical implantation more difficult. The added electronic circuitry to condition the sensor signals adds complexity, cost, and power consumption to the implanted system. The requirement to process the conditioned data by a microcontroller within the implanted system adds further energy cost, software complexity, and the opportunity for misinterpretation of the acquired signals. The additional cost of sensing increases the volume of the implanted system and increases its power budget, requiring larger batteries and longer recharge times. All of these issues are favorably resolved using a system comparable to the one described by the invention herein—no sensors are required, no sensor conditioning electronics are required, no analysis algorithms are required, and no additional energy or volume are dedicated to sensing and analysis functions.

Problems with Stimulating Whole Hypoglossal Nerve and its Distal Branches

It was previously assumed by early investigators that stimulation of the entire Hypoglossal nerve would result in useful tongue motion despite the likelihood that the Hypoglossal nerve contains nerve fibers that innervate both the tongue's agonistic and antagonistic muscles. The stimulation of the entire Hypoglossal nerve resulted in only modest changes in the airway, but which were sufficient when they occurred at the right time in the breathing cycle. This observation drove the design of electrical stimulation systems for OSA that required detection of the breathing cycle to time the delivery of stimulation. Others have chosen to stimulate more distal branches of the Hypoglossal nerve in the hopes that if stimulation were applied to these more differentiated branches then only the desired tongue muscles would be activated. One problem with this latter approach is that the surgical approach to these distal branches is more difficult and the branches are progressively smaller the more distal the placement of the electrode, making the design of an appropriate electrode for such small branches more difficult and the systems used to stimulate them less robust and the opportunity for damage for these more delicate structures more likely.

Stimulating Non-Fasciculated Nerve Bundles

Neurostimulation is often performed on peripheral motor nerves. Peripheral motor nerves emanate from the ventral horns of the spinal cord and travel in bundles to various muscle groups. A single motor nerve bundle may contain many sub-groups of neurons. Some neuron sub-groups are organized into separate sub-bundles called fascicles, which are easily viewed in histological cross section, and often connect to groups of muscle fibers within the same muscle. With these sub-groups, stimulation of the sub-group typically results in activation of a group of muscles working together to achieve a desired effect.

Other peripheral nerves, such as the Hypoglossal nerve, have sub-bundles that are not organized into fascicles. Instead, these sub-bundles run in somewhat controlled but less well defined regions of the nerve, and are not easily recognizable in a cross-sectional view. These sub-groups often go to multiple muscle groups in different locations. An example of such a nerve is the Hypoglossal nerve, which has multiple sub-groups connecting to different portions of the tongue. A more detailed description of the nerve structure for the human tongue is disclosed in U.S. Patent Application No. 61/136,102, filed Oct. 9, 2008, hereby incorporated by reference in its entirety.

Not every muscle of the human tongue is involved in the opening of the airway. Some stimulated muscles act to block the airway. In the embodiments described, the only nerves targeted by the targeted selective electrical stimulation method described herein are nerves that stimulate muscles that activate the tongue resulting in the optimal opening of the airway and suppression of unwanted tongue movements. In contrast, whole nerve stimulation activates the entire nerve contents and nerve bundles containing nerve fibers to both desirable and non-desirable groups of contracting muscles are simultaneously activated. This not only leads to suboptimal levels of opening, but may also produce undesirable tongue motions. A surgical way to avoid this problem with less than optimal stimulation methods is to place stimulating electrodes on distal branches of the nerve that only innervate the desired muscle groups, a task that is difficult and potentially hazardous to the nerve.

In these cases, activation of the entire bundle from an artificial electrical stimulus results in activation of all of the muscles activated by the sub-groups within the stimulated nerve group. In the present invention, to target only the desired specific groups of fibers within a nerve bundle, exemplary embodiments use multiple nerve electrode contacts and multiple independent controlled current sources to activate only the desired sub-groups. This eliminates the problem of delivering stimulation to muscles not providing the desired tongue position.

The nerve in this region is non-fascicular, (proximal to the Styloglossus/Hyoglossus branches and distal to the ansa cervicalis branch) that is, the various nerve groups that separate distally are not isolated in the bundle as fascicles, but are present en masse with all of the fibers of the Hypoglossal nerve. As described in the rat dye studies above, and in studies on human cadavers, there appears, however, to be an organization to the bundle, with fibers mostly innervating the Genioglossus muscle residing in the medial region of the bundle. Studies conducted in rats, an animal model identified thus far that replicates the non-fascicular nature of the human Hypoglossal nerve, revealed an organization of the whole nerve, suggesting that targeted activation of a sub-population of neurons in the Hypoglossal nerve would be possible. Stimulation studies in rats and humans with multipolar electrodes and multiple independent current sources verified this with the result that multiple distinct motions and positions of the tongue could be achieved using targeted stimulation methods and devices. Placement of electrode contacts about the perimeter of the Hypoglossal nerve at this region has achieved targeted selective activation of the tongue muscles. The resulting airway changes elicited by stimulation depend upon which electrode contacts are activated.

In one exemplary system, an electrode 1064 is implanted around the Hypoglossal nerve at or near an approximately 1 cm length of 3.5 to 4.5 mm diameter nerve bundles. This is typically at the rear of and below the mandible, just underneath the sub-mandibular gland, proximal to the Styloglossus/Hyoglossus branches and distal to the ansa cervicalis branch. At this point, the major branches to the various tongue muscles are distal to the electrode site.

Targeted Selective Stimulation of Hypoglossal Nerve Efferents

In one embodiment, the present invention is directed to the targeted selective stimulation of Hypoglossal nerve efferents in animals. In one embodiment, the present invention is directed to the targeted selective stimulation of Hypoglossal nerve efferents in mammals. In one embodiment, the present invention is directed to the targeted selective stimulation of Hypoglossal nerve efferents in rats. In one embodiment, the present invention is directed to the targeted selective stimulation of Hypoglossal nerve efferents in humans.

In one embodiment, the present invention is directed to the targeted selective stimulation of Hypoglossal nerve efferents via electric signals emitted from at least one programmable electrode contact. In one embodiment, the targeted selective stimulation of Hypoglossal nerve efferents occurs via multiple electrode contacts. In one embodiment, the targeted selective stimulation of Hypoglossal nerve efferents is driven by multiple current sources. In one embodiment, the multiple electrode contacts are each driven by their own independent current source.

In one embodiment, the multiple electrode contacts each activate a beneficial muscle group and alternate in their operation such that the beneficial function is maintained by at least one group at all times. In one embodiment, the multiple electrode contacts each activate a beneficial muscle group and interleave their operation such that the patency of the airway is maintained. In one embodiment, the multiple electrode contacts each activate a beneficial muscle, and alternate in their operation such that the patency of the airway is maintained. In one embodiment, the multiple electrode contacts each activate one of a beneficial muscle, and interleave their operation such that the patency of the airway is maintained.

In one embodiment, the method includes activating the ipsilateral Geniohyoid muscle. In one embodiment, the method includes activating rostral or caudal or both compartments of the ipsilateral Geniohyoid muscle. In one embodiment, the method includes activating at least one compartment or both compartments of ipsilateral or with the rostral compartment of the contralateral Geniohyoid muscles increasing the dilation (of the pharyngeal airway) and the patency of the airway channel.

In one embodiment, the modulating electric signals have a frequency sufficient for a smooth tetanic contraction. In one embodiment, the modulating electric signals have a stimulation frequency of about 10 to about 40 pps. In one embodiment, the modulating electric signals are of an intensity from about 10 to about 3000 microamps ($\mu A$). In one embodiment, the modulating electric signals have a stimulation pulse width of about 10 to about 1000 microseconds ($\mu s$).

In one embodiment, the targeted selective stimulation of Hypoglossal nerve efferents activates at least one lingual muscle. In one embodiment, the targeted selective stimulation of Hypoglossal nerve efferents activates at least one upper airway channel dilator muscle. In one embodiment, at least one protrusor muscle is activated. In one embodiment, at least one protrusor muscle and at least one retrusor muscle are alternately activated. In one embodiment, at least one protrusor muscle and at least one retrusor muscle are co-activated. In one embodiment, the at least one protrusor muscle 400 activated is the genioglossus muscle. In one embodiment, at least one beneficial muscle group is activated. In one embodiment, at least two beneficial muscle groups are activated.

Method of Treating a Neurological Disorder Including Obstructive Sleep Apnea

In one embodiment, the present invention is directed to a method of treating, controlling, or preventing a neurological disorder by attaching at least one programmable electrode to a patient's Hypoglossal nerve proper 322; and selectively applying electric signals to motor efferents located within the Hypoglossal nerve proper 322 through the programmable electrode 1064 to selectively stimulate at least one muscle. In one embodiment, the electric signals are modulating. In one embodiment, the method of treating, controlling, or preventing a neurological disorder consists essentially of the recruitment of retrusor motor efferents. In one embodiment, the method comprises the recruitment of protrusor motor efferents. In one embodiment, the method comprises the recruitment of a ratio of retrusor to protrusor motor efferents such as the ratios described above to treat a neurological disorder.

In one embodiment, the neurological disorder suitable for treatment, control, or prevention by the present invention is selected from the group consisting of, but not limited to oral myofunctional disorders, atrophies, weakness, tremors, fasciculations, and myositis.

In one embodiment, the neurological disorder is obstructive sleep apnea. Other potential applications of this method, in addition to treatment of obstructive sleep apnea, include, for example, supplemental nerve stimulation to keep the airway open for treatment of snoring, hypopnea, or countering motor activation of the tongue during a seizure. Other health problems related to the patency of a patient's airway may also be treated using methods provided by the present invention.

In one embodiment, the present invention provides a method of treating, controlling, or preventing obstructive sleep apnea including the steps of attaching at least one programmable electrode to a patient's Hypoglossal nerve proper 322; and selectively applying electric signals to motor efferents located within the patient's Hypoglossal nerve proper 322 through the programmable electrode 1064 to selectively stimulate at least one muscle. In one embodiment, at least one programmable electrode 1064 provides a continuous, low level electrical stimulation to specific motor efferents to maintain the stiffness of the upper airway channel throughout the respiratory cycle. In one embodiment, at least one programmable electrode provides intermittent electrical stimulation to specific motor efferents at controlled, predetermined intervals sufficiently close to achieve a constantly opened airway.

In one embodiment, the method of treating, controlling, or preventing obstructive sleep apnea includes selectively activating one or more muscles in the upper airway channel to effectively reduce the severity of obstructive sleep apnea and improve airway patency. In one embodiment, the method includes targeted selective stimulation of motor efferents that activate the geniohyoid muscle, causing anterosuperior movement of the hyoid bone to increase the patency of the upper airway channel. In one embodiment, the method includes targeted selective stimulation of functionally opposite muscles that also effectively stiffen the upper airway channel to reduce the risk of collapse.

In one embodiment, the method of treating, controlling, or preventing obstructive sleep apnea consists essentially of the recruitment of protrusor motor efferents. In one embodiment, the method includes activating at least one protrusor muscle. In one embodiment, the method includes targeted selective stimulation of protrusor motor efferents located within the Hypoglossal nerve proper 22 that activate the genioglossus muscle, causing protrusion of the tongue to increase the patency of the upper airway channel.

System Programming

System programming and stimulation of the exemplary embodiments do not have to take into account the timing of respiration. When electrical stimulation is applied to a nerve bundle there are essentially two factors that determine which fibers within the bundle will be excited. The first is distance of the fiber to the contact—the closer a fiber is to the contact, the higher the current gradient and the more likely that the fiber will be excited. The second is the diameter of the fiber, which determines the voltage changes across the membrane and hence the likelihood of reaching the threshold of generating an action potential—the larger the diameter, the more likely that the fiber will be excited. At a particular current amplitude of sufficient duration, all of the fibers within a certain distance or diameter of the stimulation will be excited. As current amplitude increases, more fibers will be excited. Since each fiber is associated with a muscle fiber or fibers (jointly referred to as a motor unit), as more nerve fibers are excited, more muscle fibers are caused to contract, causing a gradation in force production or position as the stimulation current or phase duration is increased. The point at which this force is first generated is referred to as the motor threshold, and the point at which all of the fibers are all recruited is the maximum stimulation level. The comfort of this activity to the patient is often exceeded before this maximum level is attained, and it is important to determine the threshold level and the level at which the useful level of force or position is obtained at a level that is not uncomfortable for the patient. The point at which the optimal or best possible force or position is obtained is the target level.

In certain exemplary embodiments, system programming entails operatively connecting at least one electrode with a motor efferent located within a nerve (for example, the Hypoglossal nerve). This connection need not be a physical connection. The connection can be any connection known to those skilled in the art where the connection is sufficient to deliver a stimulus to the targeted motor efferent of the targeted nerve. Once the electrode is operatively connected with the targeted nerve, two or more electrode contacts are activated to determine their applicable stimulus thresholds (i.e., the threshold at which a desired response is achieved). The level of stimulation comfortable to the patient can also be measured. The contacts may also be assigned into functional groups that provide tongue motions that are beneficial in maintaining airway patency.

In certain exemplary embodiments, stimulation may be provided to the nerve using at least two functional groups. A functional group is defined as one or more electrode contacts (for example contacts 1164*a*, 1264*b*, 1264*c* and 1264*d* shown in FIG. 10) that deliver a stimulus that results in a tongue movement that maintains an open airway. Each functional group may have a single contact, or may have multiple contacts. For example, a functional group with two contacts could be used to excite a population of nerve fibers that lie between two adjacent contacts. A non-limiting example of how stimulation from the functional group can be delivered is field or current steering, described in International Patent PCT/US2008/011599, incorporated by reference in its entirety. In another exemplary embodiment, two or more adjacent contacts may be used to focus the stimulation field to limit the area of excited neurons to a smaller area than what might be achieved with a single contact using a pulse generator case as a return contact. In another exemplary embodiment, two or more non-adjacent contacts may be used together to generate a useful response that is better than the response by the single contacts alone could produce. The table below shows various exemplary combinations of functional groups for an embodiment having six contacts numbered 1-6. A single contact can be a member of more than one functional group. For example, contact two could be in two different groups—one group made up of contact 1 and 2, and another group made up of contact 2 and 3. Exemplary contact groups are shown below.

a. Single Contact Groups: 1, 2, 3, 4, 5, 6 b. Double Contact Groups: 1&2, 2&3, 3&4, 4&5, 5&6, 6&1 c. Triple Contact Groups: 1&2&3, 2&3&4, 3&4&5, 4&5&6, 5&6&1, 6&1&2 d. Non-Adjacent Contact Groups: 1&3, 2&4, 3&5, 4&6, 5&1, 1&3&5, 2&4&6, 3&5&1, FIG. 11 illustrates an exemplary stimulation strategy. As shown in FIG. 11, functional groups may be used to establish load sharing, amplitude ramping, and delayed start of stimulation to optimize the delivery of stimulation of the targeted nerve (the Hypoglossal nerve, for example). In the exemplary strategy of FIG. 13, stimulation is delayed after a patient begins a sleep session, allowing the patient to fall asleep before stimulation begins. Stimulation from each of the functional groups takes turns ramping up, holding the tongue in the desired position for a period of time that is sustainable without significant fatigue, before the next group starts and the previous group stops allowing muscle fibers associated with the previous group to relax, and which helps to prevent fatigue but which maintains desirable tongue position all the time.

The remaining effort in programming the two or more electrode contacts is to select electrode contacts and assign them to functional groups. During stimulation, only a single functional group will be on at a time or on at overlapping out of phase intervals, but a group may contain more than one contact. The effect of having more than one contact should additionally be tested to make sure that the sensation of the two contacts or groups on at the same time does not result in discomfort for the patient. Ostensibly, if a single contact results in good airway opening there is little reason to add another contact to the same targeted efferent. If the use of two contacts provides better opening then the pair should be tested together and assigned to the same group.

In certain embodiments, at least two functional groups are defined, so that the load of maintaining tongue position is shared, prolonging the time until fatigue sets in or preventing it altogether. Stimulation starts with the first group, which ramps up in amplitude to a target amplitude, stays at the target level for a pre-determined amount of time and then is replaced or overlapped by the next group. This repeats through one or more of the functional groups. The pattern may repeat beginning with the first functional group, but need not begin with the same functional group each time. In certain exemplary embodiments, the groups may be programmed to ramp up in amplitude while the previous group is still on and at the target level of the next group the first group would be programmed to terminate. This would maintain a constant, continuous level of stimulation that is shared amongst the programmed groups. The cycle repeats until the end of the sleep session.

The load of maintaining muscle tone and position is shared by all of the functional groups. In one embodiment, each contact is pulsed at different or overlapping intervals (FIGS. 14A and 14B). This prevents or minimizes fatigue by alternately resting and stimulating targeted muscle groups and thereby preventing the tongue from falling into a position that can cause apnea or hypopnea. The predetermined amount of time that a group is programmed to stay on may be determined by observing the tongue at a chosen stimulation frequency and determining how long the resulting contraction can be maintained before fatigue causes the resulting position control to degrade.

In another embodiment, each contact is pulsed at a fraction of the total target frequency (discussed below) and out of phase with each of the other contacts (FIG. 4B). For example, if the target frequency is 30 pps, each contact is pulsed at 10 pps with the other contacts interleaved between each pulse rather than pulsing each contact for an interval at 30 pps as shown in FIG. 13. In such an embodiment, the pulses are out of phase with one another so each contact pulses sequentially in a nearly continuous pattern to share the stimulation load of the contacts. Spreading the load over each of the contacts allows a much lower frequency to be used that allows for near constant muscle stimulation without or substantially without fatigue or diminished positioning.

Using multiple functional groups, in either a staggered or interleaved configuration, allows the tongue to be continuously or near-continuously stimulated, maintaining the tongue in a desired position even though each functional group only stimulates its neural population for a portion of a stimulation cycle. This exemplary method maintains continuous or near-continuous stimulation by load sharing between multiple functional groups, with each group—activating one or more desired tongue muscle. This method has the additional feature that group ramps would occur once for a sleep session and that stimulation levels would be maintained at their target levels, reducing the complexity of stimulation control.

Stimulus Ramping

FIG. 13 illustrates an exemplary stimulus ramp. In certain exemplary embodiments, a stimulus ramp is used to maximize patient comfort and/or for prevention of arousal. With a patient who is awake, stimulation producing a noticeable, smooth contraction is important. In treating a sleeping patient suffering from obstructive sleep apnea, however, achieving the smallest contraction necessary to treat the condition—without waking the patient—is important. The contraction only needs to be sufficient to move the tongue forward enough or make airway (the pharyngeal wall) tense/rigid enough to prevent an apnea event from occurring, and may not even be visible to the naked eye.

The sensation of the applied electrical pulses to the nerve, and the accompanying involuntary movement of the tongue generates is, at best, unnatural. In certain exemplary embodiments, the goal is to minimize sensation to a level acceptable to the patient. In certain exemplary embodiments, stimulus is gradually ramped up to ease the patient up to a target stimulus level. Stimulus starts at a threshold level, with stimulus magnitude slowly increasing to the target level. As is known to those skilled in the art, either stimulus magnitude or phase duration may be modulated to achieve control between the threshold and target levels.

If stimulation were immediately applied without a ramp, the stimulation could awaken or arouse the patient and adversely affect their sleep, just as an apnea event would. The exemplary embodiments of the present invention therefore employ the method of amplitude magnitude ramps at the start of stimulation to address this issue. The duration of this ramp is often several seconds long so that the change is gradual and the patient is able to adjust to the delivery of stimulation to the tissue.

In certain exemplary embodiments, an amplitude ramp of approximately 5 to 10 seconds is selected, (i.e., where stimulus increases to a desired level in 5 to 10 seconds). Stimulation is started at the threshold amplitude and slowly increased to the target amplitude until significant tongue movement is observed. Significant movement is defined as at least one movement that decreases airway resistance or results in increased airway air flow. The movement of the tongue and its affect on the airway can be observed with an endoscope placed in the nasal cavity, by use of fluoroscopy, or by observing the front of the oral cavity and the overall position of the tongue. Other ways of observing known to those skilled in the art can be used without departing from the scope of the invention. This is the operational point or targeted stimulation level that will be used if it is decided that this contact is to be included in the programmed stimulation protocol designed to affect the tongue during the sleeping session.

Frequency Adjustment

Another factor affecting the perceived comfort for the patient is the frequency of a pulsatile waveform. Stimulating at a very low frequency, such as approximately 1 to 3 pps, allows the easy identification of an amplitude threshold as distinct twitches or brief contractions of the muscle. These twitches or contractions are readily discernible, and often can be felt by the patient. Increasing the frequency to a sufficiently fast rate results in the fusion of the twitches (referred to as tetanus) and the relaxation between them into a smooth muscle contraction. This also quite often results in a sensation that is more comfortable for the patient, and is it is generally more comfortable for the patient as the frequency increases. Above a certain frequency, however, the sensation may again become uncomfortable, possibly associated with the level of work associated with the increased number of muscle contractions. This comfort level must be experimentally determined and it can vary from patient to patient. The amplitude is then increased to the target amplitude to sufficiently position the tongue as described above.

Delayed Stimulation Onset

In certain embodiments, stimulation is delayed until after a patient is asleep. By monitoring a patient in a sleep laboratory and/or by interviewing a patient's partner, it can be determined how much time is necessary to delay stimulation onset. In certain embodiments, this delay is programmed into a pulse generator. When the patient initiates a sleep session of the device, the pulse generator then waits for the programmed delay period to complete before applying stimulation to the Hypoglossal nerve. The delay for stimulation onset may also be associated with the point at which sleep apnea begins to appear in the sleep cycle of the patient. If apneas do not begin to appear until the deepest stage of sleep (rapid eye movement or REM) then it may be advantageous to delay the onset of stimulation well past the point at which the patient begins to sleep and until just before the point at which apnea becomes apparent. The stimulation may then be applied for a predetermined period of time and/or until the pulse generator is deactivated. In one embodiment, the pulse generator is activated and deactivated via a wireless remote.

Delaying stimulation onset, using frequency and/or amplitude modulation for a gradual ramp up or down to a desired stimulation all reduce the chances of arousing the patient in the middle of sleep, making tonic stimulation more likely to succeed. In certain treatment methods, sleeping medication for those patients who may be sensitive to the electrical stimulation activated movement may increase the chances of successful treatment.

In an exemplary embodiment, a stimulation amplitude threshold is determined by initially setting a low stimulation frequency between 1 and 3 pps. A typical waveform such as 200 us cathodic phase duration, 50 us interphase interval and 800 us anodic phase duration is selected (the anodic phase amplitude would then be one fourth the amplitude of the cathodic phase amplitude), and then waveform amplitude is slowly increased from approximately 0 µA up to a level at which the tongue muscle can be seen to twitch with each pulse, or when the patient begins to feel the pulsatile sensation. This is the point at which the electrical stimulation is just enough to excite fibers within the nerve bundle. This setting is noted as the threshold amplitude and stimulation is stopped.

Each contact may be further tested to see what frequency should be used for initial stimulation. Experience and literature evidence suggests that the higher the frequency, the more comfortable the sensation of electrical stimulation is for the patient. The more comfortable the stimulation, the less likely the patient will be awakened. In these exemplary embodiments, mulation starts at a frequency above the target frequency, and gradually decreases to the preferred target frequency. A preferred frequency is a frequency comfortable to the patient that produces a desired stimulus response. In one embodiment, one or more contacts deliver the target frequency at different intervals (FIGS. 13, 14A). In another embodiment, the target frequency is generally divided by the number of contacts and is spread or interleaved over the contacts (FIG. 4C).

Determining the starting frequency is performed by setting the contact stimulation parameters to those determined for target stimulation and including an amplitude ramp, typically 5 to 10 seconds. Stimulation is started and the frequency is slowly adjusted upwards, checking with the patient for comfort. It may be necessary to reduce amplitude with higher frequency in order to maintain comfort but if so, then the target frequency should be checked again at the lower amplitude to verify that it still produces a functional movement.

Once all of the contacts have been evaluated a common higher frequency should be selected which is the lowest of all of the contact frequencies. The frequency is set to the lowest contact frequency that achieves a response resulting in increased airway airflow or decreased airway resistance. Using the lowest frequency increases the time until fatigue occurs. This frequency is used as the startup frequency to be used after the delay from the beginning of the session has completed.

Exemplary Method of Use

The section below describes an exemplary method of patient use of the system. In the method described, the patient uses a remote control and charger (RCC) to operate and maintain the system. In this embodiment, the combination remote control and charger has a mini-USB connector, which charges an internal battery in the RCC. Optionally the RCC may rest in a cradle kept on the patient's nightstand. The cradle would have spring loaded contacts, which make connection to the RCC much like a cordless phone to charge the RCC battery. The cradle may also use a mini-USB connector to attach to a wall mounted power supply.

To start a sleep session the patient uses the RCC to activate the implantable pulse generator (IPG). In certain embodiments, the patient first activates the RCC, which then attempts to communicate to the IPG. If the RCC is unable to communicate with the IPG, the RCC indicates to the patient (by, for example, beeping three times and illuminating an LED) that it could not communicate with the IPG. This might mean that the IPG is so low in battery power that it needs to be charged, or that the RCC is not close enough to communicate to the IPG. If the IPG needs charging then the patient would attach a charge coil and cable to the RCC, place the coil over the IPG, press the charge switch on the RCC and charge the IPG until it has enough energy to stimulate, up to two or three hours for a completely depleted IPG.

If the IPG has enough energy to communicate and is in range of the RCC, then the RCC would acquire the stimulation status and battery level. Assuming that this is the start of a normal sleep session the IPG would have been in the "Stimulation Off" state. The RCC then reports the battery status by indicating the battery LED in the green state for full, amber for medium and red for low. If the battery level is full or medium then the IPG would be instructed to start asleep session and the IPG On/Off LED would be set to green. If the battery were low then the IPG would be instructed to stay off and the IPG On/Off LED would be set to red. The patient could then charge the IPG to use for one or more sleep sessions.

Once a sleep session starts, the IPG initiates a startup delay period allowing the patient to fall asleep before stimulation starts. At the end of this delay, stimulation starts with the first functional group, ramping amplitude from threshold to target amplitude and then holding for the remainder of its On-Time duration. In interleaved or staggered mode, all groups would start simultaneously, utilizing their individual ramp up parameters, then maintain stimulation levels at the target levels for the duration of the sleep period. At the beginning of stimulation, the stimulation frequency is set to the startup frequency determined during programming. This frequency would be ramped downwards to the target frequency for a programmed duration after which the target frequency is used.

It will be appreciated by those skilled in the art that changes could be made to the exemplary embodiment shown and described above without departing from the broad inventive concept thereof. It is understood, therefore, that this invention is not limited to the exemplary embodiment shown and described, but it is intended to cover modifications within the spirit and scope of the present invention as defined by the claims. For example, "an embodiment," and the like, may be inserted at the beginning of every sentence herein where logically possible and appropriate such that specific features of the exemplary embodiment may or may not be part of the claimed invention and combinations of disclosed embodiments may be combined. Unless specifically set forth herein, the terms "a", "an" and "the" are not limited to one element but instead should be read as meaning "at least one".

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method for controlling a position of a patient's tongue, the method comprising:
   implanting an electrode having a plurality of contacts, the plurality of contacts being proximate a Hypoglossal nerve;
   implanting an implantable pulse generator (IPG), the IPG being electronically coupled to the electrode;
   programming the IPG, independent of respiration, to deliver at least two electric signals to the plurality of contacts; and
   applying the at least two electric signals via the plurality of contacts to at least two targeted motor efferent groups located within the Hypoglossal nerve to stimulate at least two muscles of the tongue,
   wherein applying the at least two electric signals includes driving each contact by their own independent current source.

2. The method of claim 1, wherein programming the IPG includes assigning each contact to one of a plurality of functional groups.

3. The method of claim 2, wherein programming the IPG includes sequencing or interleaving the plurality of functional groups.

4. The method of claim 2, wherein programming the IPG includes ramping an amplitude of at least one electric signal of a first functional group of the plurality of functional groups from an initial level up to a target amplitude.

5. The method of claim 2, wherein programming the IPG includes keeping an amplitude of the at least one electric signal of the first functional group at a target amplitude for a pre-determined amount of time and then replacing the at least one electric signal of the first functional group with an at least one electric signal of a second functional group of the plurality of functional groups.

6. The method of claim 5, wherein a period of the at least one electric signal of the first functional group partially overlaps with a period of the at least one electric signal of the second functional group.

7. The method of claim 5, wherein a period of the at least one electric signal of the first functional group does not overlap with a period of the at least one electric signal of the second functional group.

8. The method of claim 5, wherein programming the IPG includes ramping an amplitude of the at least one electric signal of the second functional group from an initial level up to a target amplitude.

9. The method of claim 1, wherein programming the IPG includes sharing a generally level amount of stimulation between the plurality of contacts.

10. The method of claim 1, wherein programming the IPG includes pulsing each contact at different or overlapping intervals.

11. The method of claim 1, wherein the electrode includes a cuff housing and wherein implanting the electrode includes wrapping the cuff housing around a portion of the Hypoglossal nerve.

12. The method of claim 1, wherein the at least two electric signals are applied to the Hypoglossal nerve via an open loop system.

13. The method of claim 1 further comprising:

initiating a therapy session, wherein the applying the at least two electric signals is delayed for a predetermined amount of time after initiating the therapy session.

* * * * *